United States Patent
Perry

(10) Patent No.: US 12,188,080 B2
(45) Date of Patent: Jan. 7, 2025

(54) COMPOSITIONS AND METHODS FOR ISOLATION OF CELL-FREE DNA

(71) Applicant: Enumera Molecular, Inc., Ann Arbor, MI (US)

(72) Inventor: Jeffrey Perry, Ann Arbor, MI (US)

(73) Assignee: Enumera Molecular, Inc., Ann Arbor, MI (US)

(*) Notice: Subject to any disclaimer, the term of this patent is extended or adjusted under 35 U.S.C. 154(b) by 111 days.

(21) Appl. No.: 18/303,536

(22) Filed: Apr. 19, 2023

(65) Prior Publication Data

US 2023/0272455 A1  Aug. 31, 2023

Related U.S. Application Data

(60) Division of application No. 17/507,373, filed on Oct. 21, 2021, now Pat. No. 11,667,955, which is a continuation of application No. PCT/US2021/051355, filed on Sep. 21, 2021.

(60) Provisional application No. 63/081,308, filed on Sep. 21, 2020.

(51) Int. Cl.
*C12Q 1/68* (2018.01)
*C12Q 1/6806* (2018.01)
*C12Q 1/6834* (2018.01)

(52) U.S. Cl.
CPC ......... *C12Q 1/6806* (2013.01); *C12Q 1/6834* (2013.01); *C12Q 2537/16* (2013.01); *C12Q 2600/16* (2013.01)

(58) Field of Classification Search
CPC .................................................. C12Q 1/6813
See application file for complete search history.

(56) References Cited

U.S. PATENT DOCUMENTS

| | | | |
|---|---|---|---|
| 5,011,769 A | 4/1991 | Duck et al. |
| 5,124,246 A | 6/1992 | Urdea et al. |
| 5,288,609 A | 2/1994 | Engelhardt et al. |
| 5,403,711 A | 4/1995 | Walder et al. |
| 5,409,818 A | 4/1995 | Davey et al. |
| 5,432,272 A | 7/1995 | Benner |
| 5,624,802 A | 4/1997 | Urdea et al. |
| 5,660,988 A | 8/1997 | Duck et al. |
| 5,710,264 A | 1/1998 | Urdea et al. |
| 5,792,614 A | 8/1998 | Western et al. |
| 5,817,921 A | 10/1998 | Tom et al. |
| 5,846,717 A | 12/1998 | Brow et al. |
| 5,849,481 A | 12/1998 | Urdea et al. |
| 5,851,770 A | 12/1998 | Babon et al. |
| 5,866,337 A | 2/1999 | Schon |
| 5,882,867 A | 3/1999 | Ullman et al. |
| 5,912,340 A | 6/1999 | Kutyavin et al. |
| 5,914,230 A | 6/1999 | Liu et al. |
| 5,942,391 A | 8/1999 | Zhang et al. |
| 5,958,692 A | 9/1999 | Cotton et al. |
| 5,985,557 A | 11/1999 | Prudent et al. |
| 5,994,069 A | 11/1999 | Hall et al. |
| 6,001,567 A | 12/1999 | Brow et al. |
| 6,001,983 A | 12/1999 | Benner |
| 6,013,170 A | 1/2000 | Meade |
| 6,027,889 A | 2/2000 | Barany et al. |
| 6,037,120 A | 3/2000 | Benner |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,127,121 A | 10/2000 | Meyer, Jr. et al. |
| 6,140,496 A | 10/2000 | Benner |
| 6,143,496 A | 11/2000 | Brow et al. |
| 6,143,877 A | 11/2000 | Meyer et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,391,559 B1 | 5/2002 | Brow et al. |
| 6,399,397 B1 | 6/2002 | Zarling et al. |
| 6,440,706 B1 | 8/2002 | Vogelstein et al. |
| 6,558,928 B1 | 5/2003 | Landegren |
| 6,753,147 B2 | 6/2004 | Vogelstein et al. |

(Continued)

FOREIGN PATENT DOCUMENTS

| WO | WO 02/070755 | 9/2002 |
|---|---|---|
| WO | WO 2015/083002 | 6/2015 |

(Continued)

OTHER PUBLICATIONS

International Search Report and Written Opinion for PCT/US2021/051355. Mailed Dec. 27, 2021. 12 pages.
ABCAM product datasheet. Anti-ds DNA antibody [3519 DNA] ab27156. retrieved Sep. 16, 2020. 5 pages.
Ali et al., Rolling circle amplification: a versatile tool for chemical biology, materials science and medicine. Chem Soc Rev. May 21, 2014;43(10):3324-41.
Banér et al., Signal amplification of padlock probes by rolling circle replication. Nucleic Acids Res. Nov. 15, 1998;26(22):5073-8.

(Continued)

*Primary Examiner* — Kenneth R Horlick

(74) *Attorney, Agent, or Firm* — Casimir Jones, S.C.; Mary Ann D. Brow

(57) ABSTRACT

Provided herein are compositions and methods for isolating cell-free nucleic acid, e.g., cell-free DNA, from a sample. In particular embodiments, provided herein are compositions and methods using anti-dsDNA antibodies for isolating cell-free DNA from a sample, and for providing a sample of isolated cell-free DNA, e.g., for a nucleic acid assay. In particular embodiments, the technology relates to providing cell-free DNA from a maternal sample that is enriched for fetal cell-free fetal DNA.

14 Claims, 4 Drawing Sheets

(56) References Cited

U.S. PATENT DOCUMENTS

| | | |
|---|---|---|
| 6,852,487 B1 | 2/2005 | Barany et al. |
| 6,858,412 B2 | 2/2005 | Willis et al. |
| 6,872,816 B1 | 3/2005 | Hall et al. |
| 7,320,860 B2 | 1/2008 | Landegren et al. |
| 7,351,528 B2 | 4/2008 | Landegren |
| 7,459,315 B2 | 12/2008 | Brown |
| 7,888,017 B2 | 2/2011 | Quake et al. |
| 8,361,720 B2 | 1/2013 | Oldham-Haltom et al. |
| 8,715,937 B2 | 5/2014 | Zou et al. |
| 8,916,344 B2 | 12/2014 | Zou et al. |
| 9,057,730 B2 | 6/2015 | Mir |
| 9,096,893 B2 | 8/2015 | Allawi et al. |
| 9,212,392 B2 | 12/2015 | Allawi et al. |
| 9,376,677 B2 | 6/2016 | Mir |
| 9,481,883 B2 | 11/2016 | Mir |
| 9,556,429 B2 | 1/2017 | Mir |
| 10,465,245 B2 | 11/2019 | Mann et al. |
| 2001/0036634 A1 | 3/2001 | Chow et al. |
| 2002/0051986 A1 | 5/2002 | Baez et al. |
| 2002/0108908 A1* | 8/2002 | Watson, III ............ B01J 20/321 210/321.6 |
| 2008/0254474 A1 | 10/2008 | Laird et al. |
| 2011/0171640 A1 | 7/2011 | Bhatt et al. |
| 2019/0144848 A1 | 5/2019 | De Carvalho et al. |
| 2020/0248272 A1 | 8/2020 | Kennedy et al. |
| 2020/0261639 A1 | 8/2020 | Surkov |

FOREIGN PATENT DOCUMENTS

| | | |
|---|---|---|
| WO | WO 2017/020023 | 2/2017 |
| WO | WO 2017/020024 | 2/2017 |
| WO | WO 2017/083366 | 5/2017 |
| WO | WO 2017/087560 | 5/2017 |
| WO | WO 2018/094031 | 5/2018 |
| WO | WO 2019/053243 | 3/2019 |
| WO | WO 2019/158726 | 8/2019 |
| WO | WO 2019/195346 | 10/2019 |
| WO | WO 2020/206170 | 10/2020 |
| WO | WO 2021/064463 | 4/2021 |

OTHER PUBLICATIONS

Barany. Genetic disease detection and DNA amplification using cloned thermostable ligase. Proc Natl Acad Sci U S A. Jan. 1, 1991;88(1):189-93.

Brewster et al., Copy number imbalances between screen- and symptom-detected breast cancers and impact on disease-free survival. Cancer Prev Res (Phila). Oct. 2011;4(10):1609-16.

Burmester et al., DMET microarray technology for pharmacogenomics-based personalized medicine. Methods Mol Biol. 2010;632:99-124.

Caldwell et al., CYP4F2 genetic variant alters required warfarin dose. Blood. Apr. 15, 2008;111(8):4106-12.

Ceska et al., Structure-specific DNA cleavage by 5' nucleases. Trends Biochem Sci. Sep. 1998;23(9):331-6.

Chan et al., Size distributions of maternal and fetal DNA in maternal plasma. Clin Chem. Jan. 2004;50(1):88-92.

Corstjens et al., Infrared up-converting phosphors for bioassays. IEE Proc Nanobiotechnol. Apr. 2005;152(2):64-72.

Daly et al., Multiplex assay for comprehensive genotyping of genes involved in drug metabolism, excretion, and transport. Clin Chem. Jul. 2007;53(7):1222-30.

Deeken et al., A pharmacogenetic study of docetaxel and thalidomide in patients with castration-resistant prostate cancer using the DMET genotyping platform. Pharmacogenomics J. Jun. 2010;10(3):191-9.

Deeken et al., The Affymetrix DMET platform and pharmacogenetics in drug development. Curr Opin Mol Ther. Jun. 2009;11(3):260-8.

Dennis Lo et al., Maternal plasma DNA sequencing reveals the genome-wide genetic and mutational profile of the fetus. Sci Transl Med. Dec. 8, 2010;2(61):61ra91. 15 pages.

Doty et al., Strand Separation and Specific Recombination in Deoxyribonucleic Acids: Physical Chemical Studies. Proc Natl Acad Sci U S A. Apr. 1960;46(4):461-76.

Dumaual et al., Comprehensive assessment of metabolic enzyme and transporter genes using the Affymetrix Targeted Genotyping System. Pharmacogenomics. Mar. 2007;8(3):293-305.

Feederle et al., Antibodies specific for nucleic acid modifications. RNA Biology, 2017. vol. 14, No. 9, 1089-1098.

Geiersbach et al., Unknown partner for USP6 and unusual SS18 rearrangement detected by fluorescence in situ hybridization in a solid aneurysmal bone cyst. Cancer Genet. Apr. 2011;204(4):195-202.

Gossett et al., DNA Immunoprecipitation (dip) for the determination of DNA-Binding specificity. CSH protocols, 2008, vol. 3, Iss 3. 5 pages.

Grunt et al., Clinical relevance of size selection of circulating DNA. Transl Cancer Res 2018;7(Suppl 2):S171-S184.

Hall et al., Sensitive detection of DNA polymorphisms by the serial invasive signal amplification reaction. Proc Natl Acad Sci U S A. Jul. 18, 2000;97(15):8272-7.

Hardenbol et al., Highly multiplexed molecular inversion probe genotyping: over 10,000 targeted SNPs genotyped in a single tube assay. Genome Res. Feb. 2005;15(2):269-75.

Hardenbol et al., Multiplexed genotyping with sequence-tagged molecular inversion probes. Nat Biotechnol. Jun. 2003;21(6):673-8.

Holdenrieder et al., Cell-Free DNA in serum and plasma: Comparison of ELISA and Quantitative PCR. Clinical Chemistry, 2005, 51, No. 8. 1544-1546.

Hu et al., An enrichment method to increase cell-free fetal DNA fraction and significantly reduce false negatives and test failures for non-invasive prenatal screening: a feasibility study. J Transl Med. Apr. 11, 2019;17(1):124.

Ji et al., Molecular inversion probe analysis of gene copy alterations reveals distinct categories of colorectal carcinoma. Cancer Res. Aug. 15, 2006;66(16):7910-9.

Kaiser et al., A comparison of eubacterial and archaeal structure-specific 5'-exonucleases. J Biol Chem. Jul. 23, 1999;274(30):21387-94.

Lin et al., Synthesis and duplex stability of oligonucleotides containing cytosine-thymine analogues. Nucleic Acids Res. Dec. 25, 1989;17(24):10373-83.

Lin et al., Synthesis of oligodeoxyribonucleotides containing degenerate bases and their use as primers in the polymerase chain reaction. Nucleic Acids Res. Oct. 11, 1992;20(19):5149-52.

Liu et al., Flap endonuclease 1: a central component of DNA metabolism. Annu Rev Biochem. 2004;73:589-615.

Lyamichev et al., Polymorphism identification and quantitative detection of genomic DNA by invasive cleavage of oligonucleotide probes. Nat Biotechnol. Mar. 1999;17(3):292-6.

Man et al., Genetic variation in metabolizing enzyme and transporter genes: comprehensive assessment in 3 major East Asian subpopulations with comparison to Caucasians and Africans. J Clin Pharmacol. Aug. 2010;50(8):929-40.

Marmur et al., Strand Separation and Specific Recombination in Deoxyribonucleic Acids: Biological Studies. Proc Natl Acad Sci U S A. Apr. 1960;46(4):453-61.

McDonald et al., CYP4F2 is a vitamin K1 oxidase: An explanation for altered warfarin dose in carriers of the V433M variant. Mol Pharmacol. Jun. 2009;75(6):1337-46.

Mega et al., Cytochrome p-450 polymorphisms and response to clopidogrel. N Engl J Med. Jan. 22, 2009;360(4):354-62.

Mouliere et al., Enhanced detection of cirulating tumor DNA by fragment size analysis. Sci Transl Med. Nov. 7, 2018;10(466):eaat4921. 13 pages.

Nilsson et al., Padlock probes: circularizing oligonucleotides for localized DNA detection. Science. Sep. 30, 1994;265(5181):2085-8.

Ostermayer. Preparation and properties of infrared-to-visible conversion phosphors. Metall. Trans. 1971. 752, 747-755.

Pisetsky et al., The influence of DNA size on the bindings of antibodies to DNA in the sera of normal human subjects and paitents with systemic lupus erythematosus (SLE) Clin Exp Immunol 116:354-359, (1999) .

(56) References Cited

OTHER PUBLICATIONS

Porreco et al., Evaluation of a novel screening method for fetal aneuploidy using cell-free DNA in maternal plasma. J Med Screen. Mar. 2020;27(1):1-8.
Porreco et al., Evaluation of a novel screening method for fetal aneuploidy using cell-free DNA in maternal plasma. J Med Screen. 2020, vol. 27(1) 1-8.
Press et al., Ovarian carcinomas with genetic and epigenetic BRCA1 loss have distinct molecular abnormalities. BMC Cancer. Jan. 22, 2008;8:17.
Qiagen. QIAamp DSP Circulating NA Kit Instructions for use. Qiagen GmbH. 2019. 48 pages.
Schiffman et al., Molecular inversion probes reveal patterns of 9p21 deletion and copy number aberrations in childhood leukemia. Cancer Genet Cytogenet. Aug. 2009;193(1):9-18.
Schiffman et al., Oncogenic BRAF mutation with CDKN2A inactivation is characteristic of a subset of pediatric malignant astrocytomas. Cancer Res. Jan. 15, 2010;70(2):512-9.
Schweitzer et al., Aromatic Nonpolar Nucleosides as Hydrophobic Isosteres of Pyrimidine and Purine Nucleosides. J Org Chem. Dec. 1, 1994;59(24):7238-7242.
Schweitzer et al., Hydrophobic, Non-Hydrogen-Bonding Bases and Base Pairs in DNA. J Am Chem Soc. Feb. 22, 1995;117(7):1863-1872.
Selvin. Fluorescence resonance energy transfer. Methods Enzymol. 1995;246:300-34.
Shi et al., Size profile of cell-free Dna: A beacon guiding the practice and innovation of clinical testing. Theranostics 2020; 10(11):4737-4748.
Sissung et al., Clinical pharmacology and pharmacogenetics in a genomics era: the DMET platform. Pharmacogenomics. Jan. 2010;11(1):89-103.
Stryer et al., Fluorescence energy transfer as a spectroscopic ruler. Annu Rev Biochem. 1978;47:819-46.
Thermo Scientific. Immunoprecipitation (IP) technical guide and protocols. Pierce Biotechnology. Retrieved Sep. 21, 2020. 12 pages.
Turner et al., Massively parallel exon capture and library-free resequencing across 16 genomes. Nat Methods. May 2009;6(5):315-6.
Tyagi et al., Wavelength-shifting molecular beacons. Nat Biotechnol. Nov. 2000;18(11):1191-6.
Van De Rijke et al., Up-converting phosphor reporters for nucleic acid microarrays. Nat Biotechnol. Mar. 2001;19(3):273-6.
Vogelstein et al., Digital PCR. Proc Natl Acad Sci U S A. Aug. 3, 1999;96(16):9236-41.
Vong et al., Enrichment of fetal and maternal long cell-free DNA fragments from maternal plasma following DNA repair. Prenatal Diagnosis 2019 39: 88-99.
Wang et al., Allele quantification using molecular inversion probes (MIP). Nucleic Acids Res. Nov. 28, 2005;33(21):e183.
Wang et al., Analysis of molecular inversion probe performance for allele copy number determination. Genome Biol. 2007;8(11):R246.
Wang et al., High quality copy number and genotype data from FFPE samples using Molecular Inversion Probe (MIP) microarrays. BMC Med Genomics. Feb. 19, 2009;2:8.

\* cited by examiner

FIG. 4

| Assay | Fetal Fraction (SNP based) | Fetal Fraction (CHR Y based) | Fetal Fraction (CHR X based) | GOF | Total Reads |
|---|---|---|---|---|---|
| Standard purification | 7.424% | 11.9% | 11.8% | 1.52 | 18 million |
| Anti-dsDNA Purified cfDNA | 22.011% | 13.9% | 13.5% | 2.17 | 14 million |

COMPOSITIONS AND METHODS FOR ISOLATION OF CELL-FREE DNA

The present application is a continuation of U.S. patent application Ser. No. 17/507,373, filed Oct. 21, 2021, now U.S. Pat. No. 11,667,955, which is a continuation of PCT/US21/51355, filed Sep. 21, 2021, which claims priority to U.S. Provisional Application Ser. No. 63/081,308, filed Sep. 21, 2020, each of which is incorporated herein by reference.

FIELD OF THE INVENTION

The present invention relates to compositions and methods for isolating circulating cell-free DNA (cfDNA) from a sample, e.g., a blood sample. Specifically, provided herein are methods of using anti-dsDNA antibodies for isolating cell-free DNA from a sample, and for providing a sample of isolated cell-free DNA. In particular embodiments, the technology relates to providing cell-free DNA from a maternal sample that is enriched for cell-free fetal DNA relative to cell-free maternal DNA from the maternal sample.

BACKGROUND OF THE INVENTION

Genetic testing is an important tool used in several medial applications, including prenatal testing and the detection of genes that are associated with various disease states, including autoimmune disease, cardiovascular disease, transplant rejection, and cancer. However, conventional methods for collecting genetic material from a patient have remained largely invasive. For example, prenatal screening for genetic abnormalities typically relies on invasive procedures such as amniocentesis or chorionic villus sampling, both of which are associated with a small risk of miscarriage and/or needle damage to the developing fetus. As another example, cancer diagnosis often requires a tumor biopsy, which is an invasive and risky procedure that may in some instances not be possible.

The isolation and use of circulating, cell-free DNA (cfDNA) represents a viable alternative for non-invasive testing methods, including diagnostic methods for various disease states. For example, cfDNA may be obtained from a cancer patient and used to assess non-self (e.g., tumor) DNA, which may be used for cancer prognosis, diagnosis, response to therapy, and assessment of recurrence. However, cfDNA fragments are relatively scarce, thus impairing the widespread use of genetic tests that require adequate levels of cfDNA for accuracy. Accordingly, improved methods for isolation of cfDNA from biological samples are needed.

The isolation and use of circulating cell-free fetal DNA represents a particularly desirable alternative for non-invasive prenatal testing (NIPT) methods. cfDNA from a fetus can be obtained from the mother's blood, thus potentially eliminating the need for amniocentesis or chorionic villus sampling for certain genetic tests. However, cfDNA fragments, and in particular fetal cfDNA fragments are relatively scarce in the mother's circulation. Moreover, the accuracy of NIPT methods depends largely on the fetal fraction of cfDNA present in the sample. Accordingly, methods and compositions for enriching cell-free fetal DNA, i.e., for capturing a larger fraction of cell-free fetal DNA from a maternal sample relative to the total amount of cell-free DNA captured from the sample are needed.

SUMMARY OF THE INVENTION

The present invention provides compositions and methods for isolating cell-free DNA in a sample. In some embodiments, the present invention provides compositions and methods for isolating cell-free fetal DNA in a sample.

In some aspects, provided herein are methods for enriching cfDNA in a sample comprising contacting the sample with an anti-double-stranded deoxyribonucleic acid (dsDNA) antibody, and isolating cfDNA from the sample. The step of contacting the sample with an anti-dsDNA antibody may be performed prior to isolating the cfDNA from the sample.

Detergents used during the isolation of cfDNA allows for isolation of different membrane bound compartments. For example, using Triton X-100 solubilizes detergent sensitive membranes, but not membranes rich in cholesterol (e.g., detergent resistant membranes). Membranes are differentially solubilized in various detergents as reported in Schuck et. al., Proc. Natl. Acad. Sci. USA 100:10, the entire contents of which are incorporated herein by reference.

In some embodiments, the sample is a biological fluid. For example, the biological fluid may be blood, serum, or plasma. In some embodiments, the biological fluid is obtained from a pregnant subject. In some embodiments, the biological fluid is obtained from a patient. For example, the biological fluid may be obtained from a patient suffering from or at risk of developing a disease state including autoimmune disease, cardiovascular disease, transplant rejection, or cancer.

cfDNA may be isolated from the sample by any suitable method. In some embodiments, cfDNA is isolated using a commercially available kit.

In some embodiments, the methods provided herein result in an enriched concentration of amount of cfDNA in the sample compared with samples that are not contacted with an anti-dsDNA antibody. In some embodiments, the methods provided herein result in an enriched concentration or amount of fetal cfDNA in the sample compared to samples that are not contacted with an anti-dsDNA antibody.

In some embodiments, the methods for enriching cfDNA described herein may be performed and the enriched cfDNA may be subsequently subjected to methods for genetic analysis. Genetic analysis may include analysis of any desired genetic mutation, including base substitutions, insertions, deletions, translocations, or analysis of variations in copy numbers of specific nucleic acids sequences that may arise, e.g., from variations in chromosome number, gene copy number, expression level, etc. The methods for enriching cfDNA described herein find use in assessing a subject for various disease states, including autoimmune disease, cardiovascular disease, transplant rejection, and cancer. In some embodiments, genetic analysis may include quantification of "self" and "non-self" nucleic acid, such as quantification of cfDNA derived from the subject and quantification of cfDNA derived from an allogenic transplant (e.g. for use assessing the risk of transplant rejection). In some embodiments, genetic analysis may include quantification of cfDNA derived from a tumor (e.g. circulating tumor cfDNA). For example, the enriched cfDNA obtained by a method as described herein may be used in methods of genetic screening for diagnosing and/or prognosing cancer. In some embodiments, the enriched fetal cfDNA fraction obtained by a method as described herein may be used in methods of genetic screening, e.g., prenatal testing, particularly for non-invasive prenatal testing (NIPT). NIPT is directed to the analysis of cell-free DNA (cfDNA) from a fetus that circulates in the blood of a woman carrying the fetus in utero.

In some embodiments, the technology provides:
1. A method for capturing cell-free DNA from a sample, comprising:
   a) contacting a sample with a composition comprising an exogenous anti-dsDNA antibody to form an antibody-DNA complex comprising the anti-dsDNA antibody and cell-free DNA;
   b) separating the antibody-DNA complex from the sample to provide captured cell-free DNA.
2. The method of embodiment 1, further comprising a step c) of releasing captured cell-free DNA from the antibody-DNA complex.
3. The method of embodiment 1, further comprising assaying the captured cell-free DNA.
4. The method of embodiment 3, wherein the assaying comprises adding captured cell-free DNA to a reaction mixture.
5. The method of embodiment 4, wherein adding captured cell-free DNA to a reaction mixture comprises adding the antibody-DNA complex to the reaction mixture.
6. The method of embodiment 4, wherein the reaction mixture comprises a nucleic acid-modifying enzyme, preferably a nucleic acid-modifying enzyme selected from a nucleic acid polymerase, a nuclease, and a ligase.
7 The method of embodiment 1, wherein the captured cell-free DNA comprises cell-free fetal DNA.
8. The method of embodiment 1, wherein the cell-free DNA a plurality of dsDNA fragments having lengths of fewer than 500 bp, preferably fewer than 300 bp.
9. The method of embodiment 8, wherein the cell-free DNA comprises a plurality of dsDNA fragments having lengths of between 50 and 200 bp.
10. The method of embodiment 9, wherein the plurality of dsDNA fragments has a size distribution comprising peaks at about 143 bp and 166 bp.
11. The method of embodiment 1, wherein the sample comprises a biological fluid isolated from a subject.
12. The method of embodiment 11, wherein the biological fluid comprises blood or a blood product.
13. The method of embodiment 12, wherein the blood product comprises plasma.
14. The method of embodiment 11, wherein the subject is a pregnant subject, or a subject suspected of having a tumor.
15. A composition comprising an antibody-DNA complex comprising:
   a) an exogenous anti-dsDNA antibody and
   b) cell-free DNA from a sample from a subject.
16. The composition of embodiment 15, wherein the sample comprises a biological fluid from the subject.
17. The composition of embodiment 16, wherein the biological fluid comprises blood or a blood product.
18. The composition of embodiment 15, wherein the cell-free DNA comprises cell-free fetal DNA.
19. The composition of embodiment 15, wherein the antibody-DNA complex is substantially free of a biological fluid from a subject.
20. The composition of embodiment 15, wherein the antibody-DNA complex is in a buffer.
21. The composition of embodiment 15, wherein the antibody-DNA complex is in a reaction mixture.
22. The composition of embodiment 21, wherein the reaction mixture comprises a nucleic acid-modifying enzyme.
23. The composition of embodiment 22, wherein the reaction mixture comprises one or more of a nucleic acid polymerase, a nuclease, and a ligase.
24. The composition of embodiment 15, wherein the composition further comprises a solid support.
25. The composition of embodiment 24, wherein the solid support comprises a bead.
26. A kit or system for isolating cfDNA from a sample, the kit or system comprising an exogenous anti-dsDNA antibody.
27. The kit of system of embodiment 26, further comprising a solid support, preferably a bead.
28. The kit or system of embodiment 27, wherein the solid support comprises an antibody-binding reagent.
29. The kit or system of embodiment 28, wherein the antibody-binding reagent comprises a protein, preferably protein A, protein G, protein A/G, or protein L.
30. The kit or system of embodiment 26, further comprising one or more reagents selected from the group consisting of:
   a) a buffer;
   b) a salt;
   c) a detergent;
   d) a preservative;
   e) a protease inhibitor;
   f) a nuclease inhibitor; and
   g) nucleic acid modification reagents.
31. The method of embodiment 3 or embodiment 4, wherein adding captured cell-free DNA to a reaction mixture comprises adding the antibody-DNA complex to the reaction mixture.
32. The method of embodiment 31, wherein the reaction mixture comprises a nucleic acid-modifying enzyme, preferably a nucleic acid-modifying enzyme selected from a nucleic acid polymerase, a nuclease, and a ligase.
33. The method of any one of embodiments 31-32, wherein the captured cell-free DNA comprises cell-free fetal DNA.
34. The method of any one of embodiments 31-33, wherein the cell-free DNA a plurality of dsDNA fragments having lengths of fewer than 500 bp, preferably fewer than 300 bp.
35. The method of embodiment 34, wherein the cell-free DNA comprises a plurality of dsDNA fragments having lengths of between 50 and 200 bp.
36. The method of embodiment 35, wherein the plurality of dsDNA fragments has a size distribution comprising peaks at about 143 bp and 166 bp.
37. The method of any one of embodiments 31-36, wherein the sample comprises a biological fluid isolated from a subject.
38. The method of embodiment 37, wherein the biological fluid comprises blood or a blood product.
39. The method of embodiment 38, wherein the blood product comprises plasma.
40. The method of any one of embodiments 37-39, wherein the subject is a pregnant subject or a subject suspected of having a tumor.
41. The composition of any one of embodiments 15-17, wherein the cell-free DNA comprises cell-free fetal DNA.
42. The composition of embodiment 41, wherein the antibody-DNA complex is substantially free of a biological fluid from a subject.
43. The composition of embodiment 41 or 42, wherein the antibody-DNA complex is in a buffer.

44. The composition of any one of embodiments 41-43, wherein the antibody-DNA complex is in a reaction mixture.
45. The composition of embodiment 44, wherein the reaction mixture comprises a nucleic acid-modifying enzyme.
46. The composition of embodiment 45, wherein the reaction mixture comprises one or more of a nucleic acid polymerase, a nuclease, and a ligase.
47. The composition of any one of embodiments 15-23, wherein the composition further comprises a solid support.
48. The composition of embodiment 47, wherein the solid support comprises a bead.
49. The kit or system of any one of embodiments 26-29, further comprising one or more reagents selected from the group consisting of:
    a) a buffer;
    b) a salt;
    c) a detergent;
    d) a preservative;
    e) a protease inhibitor;
    f) a nuclease inhibitor; and
    g) nucleic acid modification reagents.

Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, molecular diagnostics, nucleic acids structure, biochemistry, medical science, or related fields are intended to be within the scope of the claims.

DEFINITIONS

To facilitate an understanding of the present invention, a number of terms and phrases are defined below:

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described unless the context clearly dictates otherwise. In addition, throughout the specification, the meaning of "a", "an", and "the" include plural references. The meaning of "in" includes "in" and "on."

The transitional phrase "consisting essentially of" as used in claims in the present application limits the scope of a claim to the specified materials or steps "and those that do not materially affect the basic and novel characteristic(s)" of the claimed invention, as discussed in In re Herz, 537 F.2d 549, 551-52, 190 USPQ 461, 463 (CCPA 1976). For example, a composition "consisting essentially of" recited elements may contain an unrecited contaminant at a level such that, though present, the contaminant does not alter the function of the recited composition as compared to a pure composition, i.e., a composition "consisting of" the recited components.

As used herein, the terms "subject" and "patient" refer to any organisms including plants, microorganisms and animals (e.g., mammals such as dogs, cats, livestock, and humans).

The term "self" as used herein in reference to nucleic acid refers to nucleic acids derived from the subject or patient from which a sample was isolated. For example, "self cfDNA" refers to cfDNA originating from the subject. The term "non-self" as used herein with reference to nucleic acid refers to nucleic acids derived from source other than the subject or patient from which the sample was isolated. For example, "non-self cfDNA" may refer to cfDNA released from an allogeneic transplant (e.g. organs, tissues, cells, etc. derived from a different subject that is transplanted into the subject from which the sample was isolated). cfDNA released from an allogeneic transplant may also be referred to as "donor-derived".

The term "sample" in the present specification and claims is used in its broadest sense. In some embodiments, the sample is a tissue sample. In some embodiments, the sample is a biological fluid such as blood, plasma, serum, saliva, urine, feces, gastrointestinal fluid, cerebral spinal fluid, pleural fluid, milk, lymph, or sputum. In particular embodiments, the sample is blood, serum, or plasma. In some embodiments, the sample is obtained from a pregnant subject. In some embodiments, the sample is obtained from a subject suspected of having a tumor. In some embodiments, the sample is obtained from a human subject.

As used herein, the term "pregnant" as used in reference to a subject refers to a subject, e.g., a woman, who is gestating a fetus or fetuses, e.g., in a uterus in the subject.

As used herein, the term "maternal sample" refers to a biological sample obtained from a pregnant subject, e.g., a woman.

As used herein, the term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal" and "fetal" as used herein in reference nucleic acids (including DNA, RNA, etc.) refer to the nucleic acids of a pregnant subject and the nucleic acids of the fetus or fetuses being carried by the pregnant subject, respectively.

As used herein, the term "corresponding to" sometimes refers to a nucleic acid sequence, e.g., a gene or a chromosome, that is present in the genome of different subjects, and which does not necessarily have the same sequence in all genomes, but serves to provide the identity rather than the genetic information of a sequence of interest, e.g., a gene or chromosome.

As used herein, the terms "cell-free" and "substantially cell-free" used in connection with a sample encompasses preparations of the sample from which cell components normally associated with the sample are removed. For example, a plasma sample is rendered substantially cell-free by removing blood cells, e.g., red cells, which are normally associated with it. In some embodiments, substantially cell-free samples are processed to remove cells that would otherwise contribute nucleic acids to the total amount of nucleic acid isolated from the sample.

As used herein, the term "cell-free DNA" ("cfDNA") as used in connection a sample, e.g., a fluid sample from a subject (e.g., urine, saliva, blood, plasma, etc.) refers to extracellular DNA (DNA other than DNA in cells) that is present in the sample and that is not within a cell found in the sample. As used in reference to blood and blood products, "cell-free DNA" is sometimes referred to as "circulating free DNA," and refers to DNA fragments that circulate in blood without being contained in cells in the blood. Similarly, "cell-free nucleic acid" refers to any nucleic acid found in a sample not within a cell found in the sample. Cell-free nucleic acid may be, but need not be, associated with other components in the sample, e.g., exosomes or other microvesicles, proteins, lipids, etc. cfDNA is not limited to any particular length of DNA or DNA fragments and in a healthy individual, cfDNA may range from fewer than 100 basepairs (bp) to over 10,000 bp in length, preferably between about 30 and 500 bp, preferably between about 50 and 400 bp, preferably between about 100 and 300 bp.

In the blood circulation, cfDNA exists mostly as nuclear, histone complexed DNA. The most common size of histone complexed DNA is ~166 bp, and while analyzing cfDNA size distribution, a specific ladder pattern of multiplies of this size can be detected in the human blood. Fragments shorter than ~166 bp can be the result of the linker trimming or the degradation of the non-nucleosomal cfDNA. The presence of a neoplasm, e.g., a tumor, in a subject can alter the size distribution of cfDNA in the subject. For example, when the distribution of fragment sizes of cfDNA from a subject with a tumor is analyzed, the distribution may show an increase in peaks for DNA having fewer than 150 bp relative to DNA from a healthy subject. See, e.g., M. Grunt, et al., *Transl Cancer Res* 2018; 7 (Suppl 2):S171-S184; and Jiping Shi, et al., Theranostics 2020; 10 (11):4737-4748, each of which is incorporated herein by reference it its entirety for all purposes.

"Cell-free fetal DNA" ("cffDNA"), as used herein, refers to extra-cellular fetal DNA that circulates in maternal blood, or that has been isolated from maternal blood. While cffDNA is not limited to any particular size, typically the majority of ccfDNA is significantly shorter than maternal cfDNA, Typically, the length of fetal cfDNA in maternal plasma is shorter than 500 bp and the major portion is shorter than 300 bp. Generally, when the distribution of fragment sizes of fetal cfDNA is analyzed, the distribution comprises peaks at about 143 bp and 166 bp, with a reduction in the 166 bp peak relative to the 143-bp peak when compared with maternal DNA. See, e.g., Y M Dennis Lo, et al., Sci Transl Med, December 8; 2 (61):61ra91 (2010), which is incorporated herein by reference in its entirety for all purposes.

As used herein, the term "fetal fraction" refers to the fraction of fetal nucleic acids, e.g., cell-free fetal DNA, that is present in a sample that comprises fetal and maternal nucleic acid, e.g., fetal and maternal cfDNA. Fetal fraction is often used to characterize the cfDNA in a mother's blood, reflecting the portion of cfDNA in the blood or in DNA isolated from the blood that is cffDNA.

As used herein, the term "substantially free" used in connection with a preparation, e.g., an isolated component of a sample, encompasses preparations from which other components normally associated with the sample are removed. For example, an isolated DNA, including DNA isolated from a sample (e.g., a bodily fluid, such as plasma) as part of an antibody-DNA complex, is termed "substantially free" of the sample or bodily fluid when any residual sample or bodily fluid, though present, does not alter the function of the isolated component as compared to a pure composition, i.e., a composition "consisting of" the recited component(s).

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

The term "chromosome-specific" as used herein refers to a sequence or feature that is found only in that particular type of chromosome.

The term "target" as used herein refers to a molecule sought to be sorted out from other molecules for assessment, measurement, or other characterization. For example, a target nucleic acid may be sorted from other nucleic acids in a sample, e.g., by probe binding, amplification, isolation, capture, etc.

The term "gene dosage" as used herein refers to the copy number of a gene, a genic region, a chromosome, or fragments or portions thereof. Normal individuals carry two copies of most genes or genic regions, one on each of two chromosomes. However, there are certain exceptions, e.g., when genes or genic regions reside on the X or Y chromosomes, or when genes sequences are present in pseudogenes.

The term "aneuploidy" as used herein refers to conditions wherein cells, tissues, or individuals have one or more whole chromosomes or segments of chromosomes either absent, or in addition to the normal euploid complement of chromosomes.

As used herein, the "sensitivity" of a given assay (or set of assays used together) refers to the percentage of samples that report a particular form or variant, e.g., a mutation, gene duplication, chromosome duplication, above a threshold value that distinguishes between samples exhibiting a variant phenotype (e.g., cancerous cells, aneuploidy) and samples exhibiting a normal or wild-type phenotype (e.g., non-cancerous cells, euploidy). In some embodiments, a "positive" is defined as a clinically-confirmed variant that reports an assay result associated with the presence of the disease or condition to be detected, and a false negative is defined as a clinically-confirmed variant that reports an assay result associated with the absence of the disease or condition. The value of sensitivity, therefore, reflects the probability that a given diagnostic assay performed on a known variant or diseased sample will produce a result indicative of the presence of the variation or disease. As defined here, the clinical relevance of a calculated sensitivity value represents an estimation of the probability that a given assay would detect the presence of a clinical condition when applied to a subject with that condition. Using the technology described herein, it may be possible to achieve a certain level of accuracy without the need for generating sequence reads. The accuracy may refer to sensitivity, it may refer to specificity, or it may refer to some combination thereof. The desired level of accuracy may be between 90% and 95%; it may be between 95% and 98%; it may be between 98% and 99%; it may be between 99% and 99.5%; it may be between 99.5% and 99.9%; it may be between 99.9% and 99.99%; it may be between 99.99% and 99.999%, it may be between 99.999% and 100%. Levels of accuracy above 95% may be referred to as high accuracy.

As used herein, the "specificity" of a given assay (or set of assays used together) refers to the percentage of normal samples that report an assay result associated with the presence of the disease or condition to be detected, and a false positive is defined as a clinically-confirmed normal sample that reports an assay result associated with the presence of the disease or condition. The value of specificity, therefore, reflects the probability that a given diagnostic assay performed on a known normal sample will produce a result indicative of the presence of the variation or disease. As defined here, the clinical relevance of the calculated specificity value represents an estimation of the probability that a given marker would detect the absence of a clinical condition when applied to a subject without that condition.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full-length coding sequence or by any portion of the coding sequence so long as the desired activity or function is retained.

The term "genic region" as used herein refers to a gene, its exons, its introns, and its regions flanking it upstream and downstream, e.g., 5 to 10 kilobases 5' and 3' of the transcription start and stop sites, respectively.

The term "genic sequence" as used herein refers to the sequence of a gene, its introns, and its regions flanking it upstream and downstream, e.g., 5 to 10 kilobases 5' and 3' of the transcription start and stop sites, respectively.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated, e.g., in the presence of nucleotides and a suitable nucleic acid polymerase. An oligonucleotide "primer" may occur naturally, may be made using molecular biological methods, e.g., purification of a restriction digest, or may be produced synthetically. In preferred embodiments, a primer is composed of or comprises DNA.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include base analogs, and comprise modified forms of deoxyribonucleotides as well as ribonucleotides, and include but are not limited to modified bases and nucleotides described in U.S. Pat. Nos. 5,432,272; 6,001,983; 6,037,120; 6,140,496; 5,912,340; 6,127,121 and 6,143,877, each of which is incorporated herein by reference in their entireties; heterocyclic base analogs based on the purine or pyrimidine ring systems, and other heterocyclic bases.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

As applied to polynucleotides, the term "substantial identity" denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence, which may include deletions or additions which total 20 percent or less of the reference sequence over the window of comparison. The reference sequence may be a subset of a larger sequence, for example, as a splice variant of the full-length sequences.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxigenin; luminogenic, phosphorescent or fluorogenic moieties; mass tags; and fluorescent dyes alone or in combination with moieties that can suppress ("quench") or shift emission spectra by fluorescence resonance energy transfer (FRET). FRET is a distance-dependent interaction between the electronic excited states of two molecules (e.g., two dye molecules, or a dye molecule and a non-fluorescing quencher molecule) in which excitation is transferred from a donor molecule to an acceptor molecule without emission of a photon. (Stryer et al., 1978, Ann. Rev. Biochem., 47:819; Selvin, 1995, Methods Enzymol., 246: 300, each incorporated herein by reference). As used herein, the term "donor" refers to a fluorophore that absorbs at a first wavelength and emits at a second, longer wavelength. The term "acceptor" refers to a moiety such as a fluorophore, chromophore, or quencher that has an absorption spectrum that overlaps the donor's emission spectrum, and that is able to absorb some or most of the emitted energy from the donor when it is near the donor group (typically between 1-100 nm). If the acceptor is a fluorophore, it generally then re-emits at a third, still longer wavelength; if it is a chromophore or quencher, it then releases the energy absorbed from the donor without emitting a photon. In some embodiments, changes in detectable emission from a donor dye (e.g. when an acceptor moiety is near or distant) are detected. In some embodiments, changes in detectable emission from an acceptor dye are detected. In preferred embodiments, the emission spectrum of the acceptor dye is distinct from the emission spectrum of the donor dye such that emissions from the dyes can be differentiated (e.g., spectrally resolved) from each other.

In some embodiments, a donor dye is used in combination with multiple acceptor moieties. In a preferred embodiment, a donor dye is used in combination with a non-fluorescing quencher and with an acceptor dye, such that when the donor dye is close to the quencher, its excitation is transferred to the quencher rather than the acceptor dye, and when the quencher is removed (e.g., by cleavage of a probe), donor dye excitation is transferred to an acceptor dye. In particularly preferred embodiments, emission from the acceptor dye is detected. See, e.g., Tyagi, et al., Nature Biotechnology 18:1191 (2000), which is incorporated herein by reference.

Labels may provide signals detectable by fluorescence (e.g., simple fluorescence, FRET, time-resolved fluorescence, fluorescence polarization, etc.), radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

In some embodiment a label comprises a particle for detection. In preferred embodiments, the particle is a phosphor particle. In particularly preferred embodiments, the phosphor particle is an up-converting phosphor particle (see, e.g., Ostermayer, F. W. Preparation and properties of infrared-to-visible conversion phosphors. Metall. Trans. 752, 747-755 [1971]). In some embodiments, rare earth-doped ceramic particles are used as phosphor particles. Phosphor particles may be detected by any suitable method, including but not limited to up-converting phosphor technology (UPT), in which up-converting phosphors transfer low energy infrared (IR) radiation to high-energy visible light. While the present invention is not limited to any particular mechanism, in some embodiments the UPT up-converts infrared light to visible light by multi-photon absorption and subsequent emission of dopant-dependent phosphorescence. See, e.g., U.S. Pat. No. 6,399,397, Issued Jun. 4, 2002 to Zarling, et al.; van De Rijke, et al., Nature Biotechnol. 19 (3):273-6 [2001]; Corstjens, et al., IEE Proc. Nanobiotechnol. 152 (2):64 [2005], each incorporated by reference herein in its entirety.

As used herein, the terms "solid support" or "support" refer to any material that provides a substrate structure to which another material can be attached. A support or substrate may be, but need not be, solid. Support materials include smooth solid supports (e.g., smooth metal, glass, quartz, plastic, silicon, wafers, carbon (e.g., diamond), and ceramic surfaces, etc.), as well as textured and porous materials. Solid supports need not be flat. Supports include any type of shape, including spherical shapes (e.g., beads). Support materials also include, but are not limited to, gels, hydrogels, aerogels, rubbers, polymers, and other porous and/or non-rigid materials.

As used herein, the terms "bead" and "particle" are used interchangeably, and refer to a small support, typically a solid support, that is capable of moving about when in a solution (e.g., it has dimensions smaller than those of the enclosure or container in which the solution resides). In some embodiments, beads may settle out of a solution when the solution is not mixed (e.g., by shaking, thermal mixing, vortexing), while in other embodiments, beads may be suspended in solution in a colloidal fashion. In some embodiments, beads are completely or partially spherical or cylindrical. However, beads are not limited to any particular three-dimensional shape. In some embodiments, beads or particles may be paramagnetic. For example, in some embodiments, beads and particles comprise a magnetic material, e.g., ferrous oxide.

A bead or particle is not limited to any particular size, and in a preparation comprising a plurality of particles, the particles may be essentially uniform in size (e.g., in diameter) or may be a mixture of different sizes. In some embodiments, beads comprise or consist of nanoparticles, e.g., particles of less than about 1000 nm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 5 nm, or 1 nm in diameter. In some embodiments, the nanoparticle beads between 5 and 20 nm average diameter.

Materials attached to a solid support, e.g., materials for immunoprecipitation, such as antibodies and antibody-binding proteins, may be attached to any portion of the solid support (e.g., may be attached to an interior portion of a porous solid support material, or to an exterior portion, or to a flat or planar portion on an otherwise non-flat (non-planar) support, or vice versa). In preferred embodiments of the technology, biological molecules such as nucleic acid or protein molecules are attached to solid supports. A biological material is "attached" to a solid support when it is affixed to the solid support through chemical or physical interaction. In some embodiments, attachment is through a covalent bond. However, attachments need not be covalent and need not be permanent. In some embodiments, an attachment may be undone or disassociated by a change in condition, e.g., by temperature, ionic change, addition or removal of a chelating agent, or other changes in the solution conditions to which the surface and bound molecule are exposed.

In some embodiments, materials are attached to a first support and are localized to the surface of a second support. For example, in some embodiments, materials that comprise a ferrous or magnetic particle may be magnetically localized to a surface or a region of a surface, such as a planar surface of a slide or well.

As used herein in reference to a support or substrate, e.g., for a coating or for attachment of a molecule, the term "surface" broadly refers to a portion of a support or substrate that is accessible for a purpose. For example, a portion of a bead or vessel or plate that is accessible to be coated, functionalized, attached to a moiety, e.g., an oligonucleotide or other macromolecule, or otherwise treated, may be considered a "surface" of the bead or plate, even if the surface is on an interior portion of the bead or vessel (e.g., within a pore, within a sintered matrix, inside a well, etc.) Similarly, a portion of a matrix that is flexible and/or porous (e.g., a hydrogel, aerogel, mesh, and that is accessible for a purpose, e.g., to be coated, functionalized, attached to a moiety, derivatized, etc., may be considered a surface of the matrix. In certain embodiments, a support may comprise a support surface, sometimes termed a first surface, which is the surface of the structural support material, e.g., in the absence of a coating or modifying layer, and may further comprise substrate surface, sometimes termed a second surface, which is the surface that is accessible for a purpose after the support surface is modified, e.g., by coating with a polymer or other coating. In some embodiments, the substrate surface comprises functional groups capable of complexing covalently or non-covalently with the one or more analytes, such as oligonucleotides or polypeptides that comprise reactive or binding groups suitable for complexing with the substrate surface functional groups.

As used herein, the term "detergent" refers any of a group of synthetic, organic, liquid or water-soluble agents that have wetting-agent and emulsifying-agent properties, and include anionic agents (e.g., sodium dodecyl sulfate, sodium lauryl sulfate, ammonium lauryl sulfate, cationic (e.g., benzalkonium chloride, cetyltrimethylammonium bromide) linear alkylbenzene sulfonates (e.g., sodium dodecylbenzene sulfonate), non-ionic (e.g., a TWEEN (e.g., polyoxyethylene (20) sorbitan-monolaurate, -monopalmitate, -monostearate, or -monooleate); TRITON (polyethylene glycol p-(1,1,3,3-tetramethylbutyl)-phenyl ether, steroid and steroidal al glycosides (e.g., saponin, digitonin); and zwitterionic (net neutral) agents such as 3-[3-cholamidopropyl) dimethylammonio]-1-propanesulfonate (CHAPS), compounds. some embodiments, a "detergent" comprises a mixture of agents, e.g., TEEPOL® detergent, comprising sodium dodecylbenzene sulfonate, sodium $C_{12}$-$C_{15}$ alcohol ether sulfate.

In some embodiments, a target molecule, e.g., a biological material, is attached to a solid support through a "spacer molecule" or "linker group." Such spacer molecules are molecules that have a first portion that attaches to the biological material and a second portion that attaches to the solid support. Spacer molecules typically comprise a chain of atoms, e.g., carbon atoms, that provide additional distance between the first portion and the second portion. Thus, when attached to the solid support, the spacer molecule permits separation between the solid support and the biological material, but is attached to both. Examples of linkers and spacers include but are not limited to carbon chains, e.g., C3 and C6 (hexanediol), 1',2'-dideoxyribose (dSpacer); photocleavable (PC) spacers; triethylene glycol (TEG); and hexaethylene glycol spacers (Integrated DNA Technologies, Inc.).

As used herein, the terms "array" and "microarray" refer a surface or vessel comprising a plurality of pre-defined loci that are addressable for analysis of the locus, e.g., to determine a result of an assay. Analysis at a locus in an array is not limited to any particular type of analysis and includes, e.g., analysis for detection of an atom, molecule, chemical reaction, light or fluorescence emission, suppression, or alteration (e.g., in intensity or wavelength) indicative of a result at that locus. Examples of pre-defined loci include a grid or any other pattern, wherein the locus to be analyzed is determined by its known position in the array pattern. Microarrays, for example, are described generally in Schena, "Microarray Biochip Technology," Eaton Publishing, Natick, MA, 2000. Examples of arrays include but are not limited to supports with a plurality of molecules non-randomly bound to the surface (e.g., in a grid or other regular pattern) and vessels comprising a plurality of defined reaction loci (e.g., wells) in which molecules or signal-generating reactions may be detected. In some embodiments, an array comprises a patterned distribution of wells that receive beads, e.g., as described above for the SIMOA technology. See also U.S. Pat. Nos. 9,057,730; 9,556,429; 9,481,883; and 9,376,677, each of which is incorporated herein by reference in its entirety, for all purposes.

As used herein, the terms "dispersed" and "dispersal" as used in reference to loci or sites, e.g., on a support or surface, refers to a collection of loci or sites that are distributed or scattered on or about the surface, wherein at least some of the loci are sufficiently separated from other loci that they are individually detectable or resolvable, one from another, e.g., by a detector such as a microscope. Dispersed loci may be in an ordered array, or they may be in an irregular distribution or dispersal, as described below.

As used herein, the term "irregular" as used in reference to a dispersal or distribution of loci or sites, e.g., on a solid support or surface, refers to distribution of loci on or in a surface in a non-arrayed manner. For example, molecules may be irregularly dispersed on a surface by application of a solution of a particular concentration that provides a desired approximate average distance between the molecules on the surface, but at sites that are not pre-defined by or addressable any pattern on the surface or by the means of applying the solution (e.g., inkjet printing). In such embodiments, analysis of the surface may comprise finding the locus of a molecule by detection of a signal wherever it may appear (e.g., scanning a whole surface to detect fluorescence anywhere on the surface). This contrasts to locating a signal by analysis of a surface or vessel only at predetermined loci (e.g., points in a grid array), to determine how much (or what type of) signal appears at each locus in the grid.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717; 5,985, 557; 5,994,069; 6,001,567; 6,090,543; and 6,872,816; Lyamichev et al., Nat. Biotech., 17:292 (1999), Hall et al., PNAS, USA, 97:8272 (2000), and U.S. Pat. No. 9,096,893, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle amplification (e.g., U.S. Pat. Nos. 6,210,884, 6,183,960 and 6,235,502, herein incorporated by reference in their entireties); the variation of rolling circle amplification called "RAM amplification" (see, e.g., U.S. Pat. No. 5,942,391, incorporated herein by reference in its entirety; NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barany Proc. Natl. Acad. Sci USA 88, 189-93 (1991)); and sandwich hybridization methods (e.g., U.S. Pat. No. 5,288,609, herein incorporated by reference in its entirety).

As used herein, the term "nucleic acid modifying enzyme" refers to an enzyme that catalyzes the modification of a nucleic acid. For example, strands of DNA are modified when extended by the action of a DNA polymerase, joined to another nucleic acid or nucleotide, or when circularized by the end joining action of a ligase enzyme, when cleaved by an endonuclease, or when fully or partially digested by a nuclease, e.g., an exonuclease. Nucleic acid modifying enzymes may recognize nucleic acids by their general structure, without limitation to the particular order of nucleotides in the nucleic acid, or the action of the nucleic acid modifying enzyme may be responsive to particular nucleotides or orders of nucleotides in a strand of nucleic acid.

The term "protein interaction" as used herein encompasses interactions e.g., ionic bonding, hydrogen bonding, van der Waal's forces, hydrophobic and hydrophilic effects, within a polypeptide strand (e.g., in folding of the strand), between polypeptide strands (e.g., in formation of quaternary structures or multi-subunit proteins), or between polypeptides and other sample components (e.g., nucleic acids, lipids, carbohydrates, etc.). Disruption of protein interactions may comprise denaturing a protein, e.g., to remove or diminish a catalytic activity, or may comprise separating a protein from another molecule with which it typically associates, e.g., in a sample.

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in U.S. Pat. No. 9,096,893, incorporated herein by reference in its entirety for all purposes. Additional amplification plus invasive cleavage detection configurations, termed the QuARTS method, are described in, e.g., in U.S. Pat. Nos. 8,361,720; 8,715,937; 8,916,344; and 9,212,392, each of which is incorporated herein by reference for all purposes. The term "invasive cleavage structure" as used herein refers to a cleavage structure comprising i) a target nucleic acid, ii) an upstream nucleic acid (e.g., an invasive or "INVADER" oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain). As used herein, the term "flap endonuclease assay" includes "INVADER" invasive cleavage assays and QuARTS assays, as described above.

As used herein, the terms "digital PCR," "single molecule PCR" and "single molecule amplification" refer to PCR and other nucleic acid amplification methods that are configured to provide amplification product or signal from a single starting molecule. Typically, samples are divided, e.g., by serial dilution or by partition into small enough portions (e.g., in microchambers or in emulsions) such that each portion or dilution has, on average as assessed according to Poisson distribution, no more than a single copy of the target nucleic acid. Methods of single molecule PCR are described, e.g., in U.S. Pat. No. 6,143,496, which relates to a method comprising dividing a sample into multiple chambers such that at least one chamber has at least one target, and amplifying the target to determine how many chambers had a target molecule; U.S. Pat. No. 6,391,559; which relates to an assembly for containing and portioning fluid; and U.S. Pat. No. 7,459,315, which relates to a method of dividing a sample into an assembly with sample chambers where the samples are partitioned by surface affinity to the chambers, then sealing the chambers with a curable "displacing fluid."

See also U.S. Pat. Nos. 6,440,706 and 6,753,147, and Vogelstein, et al., Proc. Natl. Acad. Sci. USA Vol. 96, pp. 9236-9241, August 1999. See also US 20080254474, describing a combination of digital PCR combined with methylation detection.

The term "sequencing", as used herein, is used in a broad sense and may refer to any technique known in the art that allows the order of at least some consecutive nucleotides in at least part of a nucleic acid to be identified, including without limitation at least part of an extension product or a vector insert. In some embodiments, sequencing allows the distinguishing of sequence differences between different target sequences. Exemplary sequencing techniques include targeted sequencing, single molecule real-time sequencing, electron microscopy-based sequencing, transistor-mediated sequencing, direct sequencing, random shotgun sequencing, Sanger dideoxy termination sequencing, targeted sequencing, exon sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, ion semiconductor sequencing, nanoball sequencing, nanopore sequencing, 454 sequencing, Solexa Genome Analyzer sequencing, miSeq (Illumina), HiSeq 2000 (Illumina), HiSeq 2500 (Illumina), Illumina Genome Analyzer (Illumina), Ion Torrent PGM™ (Life Technologies), MinION™ (Oxford Nanopore Technologies), real-time SMRT™ technology (Pacific Biosciences), the Probe-Anchor Ligation (cPAL™) (Complete Genomics/BGI), SOLiD® sequencing, MS-PET sequencing, mass spectrometry, and a combination thereof. In some embodiments, sequencing comprises detecting the sequencing product using an instrument, for example but not limited to an ABI PRISM® 377 DNA Sequencer, an ABI PRISM® 310, 3100, 3100-Avant, 3730, or 373OxI Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR. In certain embodiments, sequencing comprises a high throughput sequencing technique, for example but not limited to, massively parallel signature sequencing (MPSS).

As used herein, the terms "peptide," "polypeptide," and "protein" are used interchangeably in reference to a chain of two or more amino acids linked together by peptide bonds. Polypeptides may be synthetic or naturally occurring, and may be short, e.g., between two about 30 amino acid residues, or may be hundreds or thousands of amino acid residues in length. Polypeptides may be composed of the 20 main naturally-occurring amino acids, or may comprise one or more non-natural amino acids, e.g., peptide nucleic acid residues, which comprise pyrimidine or purine bases on a peptide chain backbone, or modified versions of natural amino acids (e.g., modified in the structure of the side groups).

As used herein, the term "antibody" (Ab) refers to antigen-binding immunoglobulins, and includes monoclonal antibodies (mAbs) and polyclonal Abs. The term further includes all modified forms of antibodies that have the ability to bind to an antigen, e.g., fragment antibodies (fAbs) comprising portions of an immunoglobulin structure.

As used herein, the term "immunoprecipitation" is used broadly to refer to methods of enriching or purifying a specific material or antigen (e.g., a protein or protein complex, dsDNA, RNA, DNA-RNA hybrids, or other nucleic acids, etc.) from a complex mixture, e.g., plasma, using an antibody immobilized on a support directly or indirectly (e.g., the antibody may be immobilized by binding to a protein that is attached to the support) See, e.g., "Immunoprecipitation (IP) technical guide and protocols, Tech Tip #64, Thermo Scientific TR0064.0, (2009) which is incorporated herein in its entirety for all purposes.

As used herein, the term "lectins" refers to a class of non-antibody proteins that specifically binds to sugars and to sugar moieties (e.g., sugar moieties on glycoproteins and glucolipids, or within complex carbohydrates).

As used herein, the term "reaction mixture" refers to a mixture of reagents that are capable of reacting together to produce a product in appropriate external conditions over a period of time. A reaction mixture may contain nucleic acid modification reagents, e.g., nucleic acid ligation reagents, rolling circle amplification reagents, PCR amplification reagents, flap assay reagents, the recipes for which are independently known in the art.

The term "mixture" as used herein, refers to a combination of elements, that are interspersed and not in any particular order. A mixture is heterogeneous and not spatially separable into its different constituents. Examples of mixtures of elements include a number of different elements that are dissolved or suspended in the same solution, or a combination of dissolved/suspended elements and elements attached to a solid support, wherein the elements attached to the support are accessible to the elements dissolved or suspended in a solution portion of the mixture.

As used herein, the terms "crowding agent" and "volume excluder," as used in reference to a component of a fluid reaction mixture, are used interchangeably and refer to compounds, generally polymeric compounds, that reduce available fluid volume in a reaction mixture, thereby increasing the effective concentration of reactant macromolecules (e.g., nucleic acids, enzymes, etc.) Crowding reagents include, e.g., glycerol, ethylene glycol, polyethylene glycol, ficoll, serum albumin, casein, and dextran.

As used herein, the terms "digital sequencing," "single-molecule sequencing," and "next generation sequencing (NGS)" are used interchangeably and refer to determining the nucleotide sequence of individual nucleic acid molecules. Systems for individual molecule sequencing include but are not limited to the 454 FLX™ or 454 TITANIUM™ (Roche), the SOLEXA™/Illumina Genome Analyzer (Illumina), the HELISCOPE™ Single Molecule Sequencer (Helicos Biosciences), and the SOLID™ DNA Sequencer (Life Technologies/Applied Biosystems) instruments), as well as other platforms still under development by companies such as Intelligent Biosystems and Pacific Biosystems. See also U.S. Pat. No. 7,888,017, entitled "Non-invasive fetal genetic screening by digital analysis," relating to digital analysis of maternal and fetal DNA, e.g., cfDNA.

As used herein, the term "probe" or "hybridization probe" refers to an oligonucleotide (i.e., a sequence of nucleotides), whether occurring naturally as in a purified restriction digest or produced synthetically, recombinantly or by PCR amplification, that is capable of hybridizing, at least in part, to another oligonucleotide of interest. A probe may be single-stranded or double-stranded. Probes are useful in the detection, identification and isolation of particular sequences. In some preferred embodiments, probes used in the present invention will be labeled with a "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "MIP" as used herein, refers to a molecular inversion probe (or a circular capture probe). Molecular inversion probes (or circular capture probes) are nucleic acid molecules that comprise a pair of unique polynucleotide arms that hybridize to a target nucleic acid to form a nick or gap and a polynucleotide linker (e.g., a universal backbone linker). In some embodiments, the unique polynucleotide arms hybridize to a target strand immediately adjacent to each other to form a ligatable nick (generally termed "padlock probes") while in some embodiments, one the hybridized MIP must be further modified (e.g., by polymerase extension, base excision, and/or flap cleavage) to form a ligatable nick. Ligation of a MIP probe to form a circular nucleic acid is typically indicative of the presence of the complementary target strand. In some embodiments, MIPs comprise one or more unique molecular tags (or unique molecular identifiers). In some embodiments, a MIP may comprise more than one unique molecular tags, such as, two unique molecular tags, three unique molecular tags, or more. In some embodiments, the unique polynucleotide arms in each MIP are located at the 5' and 3' ends of the MIP, while the unique molecular tag(s) and the polynucleotide linker are located internal to the 5' and 3' ends of the MIP. For example, the MIPs that are used in some embodiments of this disclosure comprise the following components: first unique polynucleotide arm—first unique molecular tag—polynucleotide linker—optional second unique molecular tag—second unique polynucleotide arm. In some embodiments, the MIP is a 5' phosphorylated single-stranded nucleic acid (e.g., DNA) molecule. See, for example, WO 2017/020023, filed Jul. 29, 2016, and WO 2017/020024, filed Jul. 29, 2016, each of which is incorporated by reference herein for all purposes.

As used herein, the terms "circular nucleic acid" and "circularized nucleic acid" as used, for example, in reference to probe nucleic acids, refers to nucleic acid strands that are joined at the ends, e.g., by ligation, to form a continuous circular strand of nucleic acid.

The unique molecular tag may be any tag that is detectable and can be incorporated into or attached to a nucleic acid (e.g., a polynucleotide) and allows detection and/or identification of nucleic acids that comprise the tag. In some embodiments the tag is incorporated into or attached to a nucleic acid during sequencing (e.g., by a polymerase). Non-limiting examples of tags include nucleic acid tags, nucleic acid indexes or barcodes, radiolabels (e.g., isotopes), metallic labels, fluorescent labels, chemiluminescent labels, phosphorescent labels, fluorophore quenchers, dyes, proteins (e.g., enzymes, antibodies or parts thereof, linkers, members of a binding pair), the like or combinations thereof. In some embodiments, particularly sequencing embodiments, the tag (e.g., a molecular tag) is a unique, known and/or identifiable sequence of nucleotides or nucleotide analogues (e.g., nucleotides comprising a nucleic acid analogue, a sugar and one to three phosphate groups). In some embodiments, tags are six or more contiguous nucleotides. A multitude of fluorophore-based tags are available with a variety of different excitation and emission spectra. Any suitable type and/or number of fluorophores can be used as a tag. In some embodiments 1 or more, 2 or more, 3 or more, 4 or more, 5 or more, 6 or more, 7 or more, 8 or more, 9 or more, 10 or more, 20 or more, 30 or more, 50 or more, 100 or more, 500 or more, 1000 or more, 10,000 or more, 100,000 or more different tags are utilized in a method described herein (e.g., a nucleic acid detection and/or sequencing method). In some embodiments, one or two types of tags (e.g., different fluorescent labels) are linked to each nucleic acid in a library. In some embodiments, chromosome-specific tags are used to make chromosomal counting faster or more efficient. Detection and/or quantification of a tag can be performed by a suitable method, machine or apparatus, non-limiting examples of which include flow cytometry, quantitative polymerase chain reaction (qPCR), gel electrophoresis, a luminometer, a fluorometer, a spectrophotometer, a suitable gene-chip or microarray analysis, Western blot, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof.

In the MIPs, the unique polynucleotide arms are designed to hybridize immediately upstream and downstream of a specific target sequence (or site) in a nucleic acid target, e.g., in an RNA, cfDNA (e.g. fetal cfDNA), or genomic nucleic acid sample. In some embodiments, hybridization of a MIP to a target sequence produces a ligatable nick without a gap, i.e., the two arms of the MIP hybridize to contiguous sequences in the target strand such that no overlap or gap is formed upon hybridization. Such zero-gap MIPs are generally termed "padlock" probes. See, e.g., M. Nilsson, et al. "Padlock probes: circularizing oligonucleotides for localized DNA detection". Science. 265 (5181): 2085-2088 (1994); J. Banér, et al., *Nucleic Acids Res.,* 26 (22):5073-5078 (1998). In other embodiments the hybridized MIP/target nucleic acid complex requires modification to produce a ligatable nick. For example, in some embodiments, hybridization leaves a gap that is filled, e.g., by polymerase extending a 3' end of the MIP, prior to ligation, while in other embodiments, hybridization forms an overlapping flap structure that must be modified, e.g., by a flap endonuclease or a 3' exonuclease, to produce a ligatable nick. In some embodiments, MIPS comprise unique molecular tags are short nucleotide sequences that are randomly generated. In some embodiments, the unique molecular tags do not hybridize to any sequence or site located on a genomic nucleic acid fragment or in a genomic nucleic acid sample. In some embodiments, the polynucleotide linker (or the backbone linker) in the MIPs are universal in all the MIPs used in embodiments of this disclosure.

In some embodiments, the MIPs are introduced to nucleic acid fragments derived from a test subject (or a reference subject) to perform capture of target sequences or sites (or control sequences or sites) located on a nucleic acid sample (e.g., a genomic DNA). In some embodiments, fragmenting aids in capture of target nucleic acid by molecular inversion probes. In some embodiments, for example, when the nucleic acid sample is comprised of cell-free nucleic acid, fragmenting may not be necessary to improve capture of target nucleic acid by molecular inversion probes. For example, in some types of samples, cell-free nucleic acid is fragmented in the sample such that further fragmentation is not necessary and may even be detrimental capture of the target nucleic acids. As described in greater detail herein, after capture of the target sequence (e.g., locus) of interest, the captured target may be subjected to enzymatic gap-filling and ligation steps, such that a copy of the target sequence is incorporated into a circle-like structure. In some embodiments, nucleic acid analogs, e.g., containing labels, haptens, etc., may be incorporated in the filled section, for use, e.g., in downstream detection, purification, or other processing steps. Capture efficiency of the MIP to the target sequence on the nucleic acid fragment can, in some embodiments, be improved by lengthening the hybridization and gap-filling incubation periods. (See, e.g., Turner E H, et al., Nat Methods. 2009 April 6:1-2.).

In some embodiments, the MIPs that are used according to the disclosure to capture a target site or target sequence comprise the following components:
first targeting polynucleotide arm—first unique targeting molecular tag—polynucleotide linker—optional second unique targeting molecular tag—second targeting polynucleotide arm.

In some embodiments, the MIPs that are used in the disclosure to capture a control site or control sequence comprise the following components:
first control polynucleotide arm—first unique control molecular tag—polynucleotide linker—optional second unique control molecular tag—second control polynucleotide arm.

MIP technology may be used to detect or amplify particular nucleic acid sequences in complex mixtures. One of the advantages of using the MIP technology is in its capacity for a high degree of multiplexing, which allows thousands of target sequences to be captured in a single reaction containing thousands of MIPs. Various aspects of MIP technology are described in, for example, Hardenbol et al., "Multiplexed genotyping with sequence-tagged molecular inversion probes," Nature Biotechnology, 21 (6): 673-678 (2003); Hardenbol et al., "Highly multiplexed molecular inversion probe genotyping: Over 10,000 targeted SNPs genotyped in a single tube assay," Genome Research, 15: 269-275 (2005); Burmester et al., "DMET microarray technology for pharmacogenomics-based personalized medicine," Methods in Molecular Biology, 632: 99-124 (2010); Sissung et al., "Clinical pharmacology and pharmacogenetics in a genomics era: the DMET platform," Pharmacogenomics, 11 (1): 89-103 (2010); Deeken, "The Affymetrix DMET platform and pharmacogenetics in drug development," Current Opinion in Molecular Therapeutics, 11 (3): 260-268 (2009); Wang et al., "High quality copy number and genotype data from FFPE samples using Molecular Inversion Probe (MIP) microarrays," BMC Medical Genomics, 2:8 (2009); Wang et al., "Analysis of molecular inversion probe performance for allele copy number determination," Genome Biology, 8 (11): R246 (2007); Ji et al., "Molecular inversion probe analysis of gene copy alternations reveals distinct categories of colorectal carcinoma," Cancer Research, 66 (16): 7910-7919 (2006); and Wang et al., "Allele quantification using molecular inversion probes (MIP)," Nucleic Acids Research, 33 (21): e183 (2005), each of which is hereby incorporated by reference in its entirety for all purposes. See also in U.S. Pat. Nos. 6,858,412; 5,817,921; 6,558,928; 7,320,860; 7,351,528; 5,866,337; 6,027,889 and 6,852,487, each of which is hereby incorporated by reference in its entirety for all purposes.

MIP technology has previously been successfully applied to other areas of research, including the novel identification and subclassification of biomarkers in cancers. See, e.g., Brewster et al., "Copy number imbalances between screen- and symptom-detected breast cancers and impact on disease-free survival," Cancer Prevention Research, 4 (10): 1609-

1616 (2011); Geiersbach et al., "Unknown partner for USP6 and unusual SS18 rearrangement detected by fluorescence in situ hybridization in a solid aneurysmal bone cyst," Cancer Genetics, 204 (4): 195-202 (2011); Schiffman et al., "Oncogenic BRAF mutation with CDKN2A inactivation is characteristic of a subset of pediatric malignant astrocytomas," Cancer Research, 70 (2): 512-519 (2010); Schiffman et al., "Molecular inversion probes reveal patterns of 9p21 deletion and copy number aberrations in childhood leukemia," Cancer Genetics and Cytogenetics, 193 (1): 9-18 (2009); Press et al., "Ovarian carcinomas with genetic and epigenetic BRCA1 loss have distinct molecular abnormalities," BMC Cancer, 8:17 (2008); and Deeken et al., "A pharmacogenetic study of docetaxel and thalidomide in patients with castration-resistant prostate cancer using the DMET genotyping platform," Pharmacogenomics, 10 (3): 191-199 (2009), each of which is hereby incorporated by reference in its entirety for all purposes.

MIP technology has also been applied to the identification of new drug-related biomarkers. See, e.g., Caldwell et al., "CYP4F2 genetic variant alters required warfarin dose," Blood, 111 (8): 4106-4112 (2008); and McDonald et al., "CYP4F2 Is a Vitamin K1 Oxidase: An Explanation for Altered Warfarin Dose in Carriers of the V433M Variant," Molecular Pharmacology, 75: 1337-1346 (2009), each of which is hereby incorporated by reference in its entirety for all purposes. Other MIP applications include drug development and safety research. See, e.g., Mega et al., "Cytochrome P-450 Polymorphisms and Response to Clopidogrel," New England Journal of Medicine, 360 (4): 354-362 (2009); Dumaual et al., "Comprehensive assessment of metabolic enzyme and transporter genes using the Affymetrix Targeted Genotyping System," Pharmacogenomics, 8 (3): 293-305 (2007); and Daly et al., "Multiplex assay for comprehensive genotyping of genes involved in drug metabolism, excretion, and transport," Clinical Chemistry, 53 (7): 1222-1230 (2007), each of which is hereby incorporated by reference in its entirety for all purposes. Further applications of MIP technology include genotype and phenotype databasing. See, e.g., Man et al., "Genetic Variation in Metabolizing Enzyme and Transporter Genes: Comprehensive Assessment in 3 Major East Asian Subpopulations with Comparison to Caucasians and Africans," Journal of Clinical Pharmacology, 50 (8): 929-940 (2010), which is hereby incorporated by reference in its entirety for all purposes.

The term "capture" or "capturing", as used herein in reference to MIP probes, refers to the binding or hybridization reaction between a molecular inversion probe and its corresponding targeting site. In some embodiments, upon capturing, a circular replicon or a MIP replicon is produced or formed. In some embodiments, the targeting site is a deletion (e.g., partial or full deletion of one or more exons). In some embodiments, a target MIP is designed to bind to or hybridize with a naturally-occurring (e.g., wild-type) genomic region of interest where a target deletion is expected to be located. The target MIP is designed to not bind to a genomic region exhibiting the deletion. In these embodiments, binding or hybridization between a target MIP and the target site of deletion is expected to not occur. The absence of such binding or hybridization indicates the presence of the target deletion. In these embodiments, the phrase "capturing a target site" or the phrase "capturing a target sequence" refers to detection of a target deletion by detecting the absence of such binding or hybridization. As used in reference to other oligonucleotides, e.g., "capture oligonucleotide" the term refers to a binding or hybridization reaction between the capture oligonucleotide and a nucleic acid to be captured, e.g., to be immobilized, removed from solution, or otherwise be manipulated by hybridization to the capture oligonucleotide.

The term "capture" or "capturing" as used in reference to isolation of cell-free nucleic acid, e.g., cfDNA, refers to binding of the cell-free nucleic acid to second agent, e.g., an oligonucleotide or an antibody, to form a complex that is separable from other components in a sample. Nucleic acids, e.g., dsDNA that forms a complex with an antibody that recognizes and binds dsDNA as a cognate antigen may be referred to as being "captured" by the antibody or "captured" in and anti-dsDNA antibody-DNA complex.

As used herein in reference to anti-dsDNA antibodies, the term "exogenous" refers to an anti-dsDNA antibody that is isolated and purified from a source other than the source or sample containing the cfDNA, or from which the cfDNA has been captured. For example, to the extent a sample collected from a subject comprises an anti-dsDNA antibody that comes from the body of the subject, e.g., produced by the immune system of the subject, or administered to the subject therapeutically, any anti-dsDNA antibody in the sample is not "exogenous" but is instead "endogenous" to that subject. An anti-dsDNA antibody included in a system or kit for isolating cfDNA from a sample is typically inherently exogenous with respect to samples from any subjects other than a subject from whom the anti-dsDNA antibody was isolated. Recombinant anti-dsDNA antibodies, e.g., antibodies expressed in microbial hosts or synthesized in vitro are considered exogenous to any sample from a human or other animal subject.

The term "MIP replicon" or "circular replicon", as used herein, refers to a circular nucleic acid molecule generated via a capturing reaction (e.g., a binding or hybridization reaction between a MIP and its targeted sequence). In some embodiments, the MIP replicon is a single-stranded circular nucleic acid molecule. In some embodiments, a targeting MIP captures or hybridizes to a target sequence or site. After the capturing reaction or hybridization, in some embodiments, a ligation reaction mixture is introduced to ligate the nick formed by hybridization of the two targeting polynucleotide arms to form single-stranded circular nucleotide molecules, i.e., a targeting MIP replicon, while in some embodiments, hybridization of the MIP leaves a gap, and a ligation/extension mixture is introduced to extend and ligate the gap region between the two targeting polynucleotide arms to form a targeting MIP replicon. In some embodiments, a control MIP captures or hybridizes to a control sequence or site. After the capturing reaction or hybridization, a ligation reaction mixture is introduced to ligate the nick formed by hybridization of the two control polynucleotide arms, or a ligation/extension mixture is introduced to extend and ligate the gap region between the two control polynucleotide arms to form single-stranded circular nucleotide molecules, i.e., a control MIP replicon. MIP replicons may be amplified through a polymerase chain reaction (PCR) to produce a plurality of targeting MIP amplicons, which are double-stranded nucleic acid molecules. MIP replicons find particular application in rolling circle amplification, or RCA. RCA is an isothermal nucleic acid amplification technique where a DNA polymerase continuously adds single nucleotides to a primer annealed to a circular template, which results in a long concatemer of single stranded DNA that contains tens to hundreds to thousands of tandem repeats (complementary to the circular template). See, e.g., M. Ali, et al. "Rolling circle amplification: a versatile tool for chemical biology, materials science and medicine". *Chemical Society Reviews.*

43 (10): 3324-3341, which is incorporated herein by reference in its entirety, for all purposes. See also WO 2015/083002, which is incorporated herein by reference in its entirety, for all purposes.

Polymerases typically used in RCA for DNA amplification are Phi29, Bst, and Vent exo-DNA polymerases, with Phi29 DNA polymerase being preferred in view of its superior processivity and strand displacement ability The term "amplicon", as used herein, refers to a nucleic acid generated via amplification reaction (e.g., a PCR reaction). In some embodiments, the amplicon is a single-stranded nucleic acid molecule. In some embodiments, the amplicon is a double-stranded nucleic acid molecule. In some embodiments, a targeting MIP replicon is amplified using conventional techniques to produce a plurality of targeting MIP amplicons, which are double-stranded nucleotide molecules. In some embodiments, a control MIP replicon is amplified using conventional techniques to produce a plurality of control MIP amplicons, which are double-stranded nucleotide molecules.

The term "probe oligonucleotide" or "flap oligonucleotide" when used in reference to a flap assay (e.g., an INVADER invasive cleavage assay), refers to an oligonucleotide that interacts with a target nucleic acid to form a cleavage structure in the presence of an invasive oligonucleotide.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archival thermophiles organisms are typical thermostable. As used herein, the term "FEN-1" refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "cleaved flap" refers to a single-stranded oligonucleotide that is a cleavage product of a flap assay.

The term "cassette," when used in reference to a flap cleavage reaction, refers to an oligonucleotide or combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect. In such embodiments, the cassette may be referred to as a "FRET cassette." See, for example, U.S. Pat. No. 9,096,893, issued Aug. 4, 2015, which is incorporated herein by reference in its entirety, for all purposes.

As used herein, the phrase "not substantially complementary" as used in reference to a probe flap or arm means that the flap portion is sufficiently non-complementary not to hybridize selectively to a nucleic acid sequence, e.g., a target nucleic acid or amplified DNA, under the designated annealing conditions or stringent conditions, encompassing the terms "substantially non-complementary" and "perfectly non-complementary."

The term "signal" as used herein refers to any detectable effect, such as would be caused or provided by a label or by action or accumulation of a component or product in an assay reaction.

As used herein, the term "detector" refers to a system or component of a system, e.g., an instrument (e.g. a camera, fluorimeter, charge-coupled device, scintillation counter, solid state nanopore device, etc.) or a reactive medium (X-ray or camera film, pH indicator, etc.), that can convey to a user or to another component of a system (e.g., a computer or controller) the presence of a signal or effect. A detector is not limited to a particular type of signal detected, and can be a photometric or spectrophotometric system, which can detect ultraviolet, visible or infrared light, including fluorescence or chemiluminescence; a radiation detection system; a charge detection system; a system for detection of an electronic signal, e.g., a current or charge perturbation; a spectroscopic system such as nuclear magnetic resonance spectroscopy, mass spectrometry or surface enhanced Raman spectrometry; a system such as gel or capillary electrophoresis or gel exclusion chromatography; or other detection system known in the art, or combinations thereof.

The term "detection" as used herein refers to quantitatively or qualitatively identifying an analyte (e.g., DNA, RNA or a protein), e.g., within a sample. The term "detection assay" as used herein refers to a kit, test, or procedure performed for the purpose of detecting an analyte within a sample. Detection assays produce a detectable signal or effect when performed in the presence of the target analyte, and include but are not limited to assays incorporating the processes of hybridization, nucleic acid cleavage (e.g., exo- or endonuclease), nucleic acid amplification, nucleotide sequencing, primer extension, nucleic acid ligation, antigen-antibody binding, interaction of a primary antibody with a secondary antibody, and/or conformational change in a nucleic acid (e.g., an oligonucleotide) or polypeptide (e.g., a protein or small peptide).

As used herein, the term "prenatal or pregnancy-related disease or condition" refers to any disease, disorder, or condition affecting a pregnant woman, embryo, or fetus. Prenatal or pregnancy-related conditions can also refer to any disease, disorder, or condition that is associated with or arises, either directly or indirectly, as a result of pregnancy. These diseases or conditions can include any and all birth defects, congenital conditions, or hereditary diseases or conditions. Examples of prenatal or pregnancy-related diseases include, but are not limited to, Rhesus disease, hemolytic disease of the newborn, beta-thalassemia, sex determination, determination of pregnancy, a hereditary Mendelian genetic disorder, chromosomal aberrations, a fetal chromosomal aneuploidy, fetal chromosomal trisomy, fetal chromosomal monosomy, trisomy 8, trisomy 13 (Patau Syndrome), trisomy 16, trisomy 18 (Edwards syndrome), trisomy 21 (Down syndrome), X-chromosome linked disorders, trisomy X (XXX syndrome), monosomy X (Turner syndrome), XXY syndrome, XYY syndrome, XYY syndrome, XXXY syndrome, XXYY syndrome, XYYY syndrome, XXXXX syndrome, XXXXY syndrome, XXXYY syndrome, XXYYY syndrome, Fragile X Syndrome, fetal growth restriction, cystic fibrosis, a hemoglobinopathy, fetal death, fetal alcohol syndrome, sickle cell anemia, hemophilia, Klinefelter syndrome, dup(17)(p11.2p1.2) syndrome, endometriosis, Pelizaeus-Merzbacher disease, dup(22)(q11.2q11.2) syndrome, cat eye syndrome, cri-du-chat syndrome, Wolf-Hirschhorn syndrome, Williams-Beuren syndrome, Charcot-Marie-Tooth disease, neuropathy with liability to pressure palsies, Smith-Magenis syndrome, neurofibromatosis, Alagille syndrome, Velocardiofacial syndrome, DiGeorge syndrome, steroid sulfatase deficiency, Prader-Willi syndrome, Kallmann syndrome, microphthalmia with linear skin defects, adrenal hypoplasia, glycerol kinase deficiency, Pelizaeus-Merzbacher disease, testis-determining factor on Y, azospermia (factor a), azospermia (factor b), azospermia (factor c), 1p36 deletion, phenylketonuria, Tay-Sachs disease, adrenal hyperplasia, Fanconi anemia, spinal muscular atrophy, Duchenne's muscular dystrophy, Huntington's disease, myotonic dystrophy, Robertsonian translocation, Angelman syndrome, tuberous sclerosis, ataxia telangieltasia, open spina bifida, neural tube defects, ventral wall defects, small-for-gestational-age, congenital cytomegalovirus, achondroplasia, Marfan's syndrome, congenital hypothyroidism, congenital toxoplasmosis, biotinidase deficiency, galactosemia, maple syrup urine disease, homocystinuria, medium-chain acyl Co-A dehydrogenase deficiency, structural birth defects, heart defects, abnormal limbs, club foot, anencephaly, arhinencephaly/holoprosencephaly, hydrocephaly, anophthalmos/microphthalmos, anotia/microtia, transposition of great vessels, tetralogy of Fallot, hypoplastic left heart syndrome, coarctation of aorta, cleft palate without cleft lip, cleft lip with or without cleft palate, oesophageal atresia/stenosis with or without fistula, small intestine atresia/stenosis, anorectal atresia/stenosis, hypospadias, indeterminate sex, renal agenesis, cystic kidney, preaxial polydactyly, limb reduction defects, diaphragmatic hernia, blindness, cataracts, visual problems, hearing loss, deafness, X-linked adrenoleukodystrophy, Rett syndrome, lysosomal disorders, cerebral palsy, autism, aglossia, albinism, ocular albinism, oculocutaneous albinism, gestational diabetes, Arnold-Chiari malformation, CHARGE syndrome, congenital diaphragmatic hernia, brachydactlia, aniridia, cleft foot and hand, heterochromia, Dwarnian ear, Ehlers Danlos syndrome, epidermolysis bullosa, Gorham's disease, Hashimoto's syndrome, hydrops fetalis, hypotonia, Klippel-Feil syndrome, muscular dystrophy, osteogenesis imperfecta, progeria, Smith Lemli Opitz symdrom, chromatelopsia, X-linked lymphoproliferative disease, omphalocele, gastroschisis, pre-eclampsia, eclampsia, pre-term labor, premature birth, miscarriage, delayed intrauterine growth, ectopic pregnancy, hyperemesis gravidarum, morning sickness, or likelihood for successful induction of labor.

In some NIPT embodiments, the technology described herein further includes estimating a fetal fraction for a sample, wherein the fetal fraction is used to aid in the determination of whether the genetic data from the test subject are indicative of an aneuploidy. Methods for determining or calculating fetal fraction are known in the art.

As used herein, the term "valid detection assay" refers to a detection assay that has been shown to accurately predict an association between the detection of a target and a phenotype (e.g. medical condition). Examples of valid detection assays include, but are not limited to, detection assays that, when a target is detected, accurately predict the phenotype medical 95%, 96%, 97%, 98%, 99%, 99.5%, 99.8%, or 99.9% of the time. Other examples of valid detection assays include, but are not limited to, detection assays that qualify as and/or are marketed as Analyte-Specific Reagents (i.e. as defined by FDA regulations) or In-Vitro Diagnostics (i.e. approved by the FDA).

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, allele frequencies, RNA expression levels, protein expression, phenotypes correlating to genotypes, etc. "Allele frequency information" refers to facts or data pertaining allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

As used herein, the term "assay validation information" refers to genomic information and/or allele frequency information resulting from processing of test result data (e.g. processing with the aid of a computer). Assay validation information may be used, for example, to identify a particular candidate detection assay as a valid detection assay.

BRIEF DESCRIPTION OF THE DRAWINGS

FIG. 4 shows a table comparing fetal cfDNA yield (fetal fraction) of cfDNA prepared using standard purification to cfDNA prepared using anti-dsDNA antibody treatment, as described herein. Fetal fraction was measured by the three methods indicated.

DETAILED DESCRIPTION OF THE INVENTION

Figure 1:
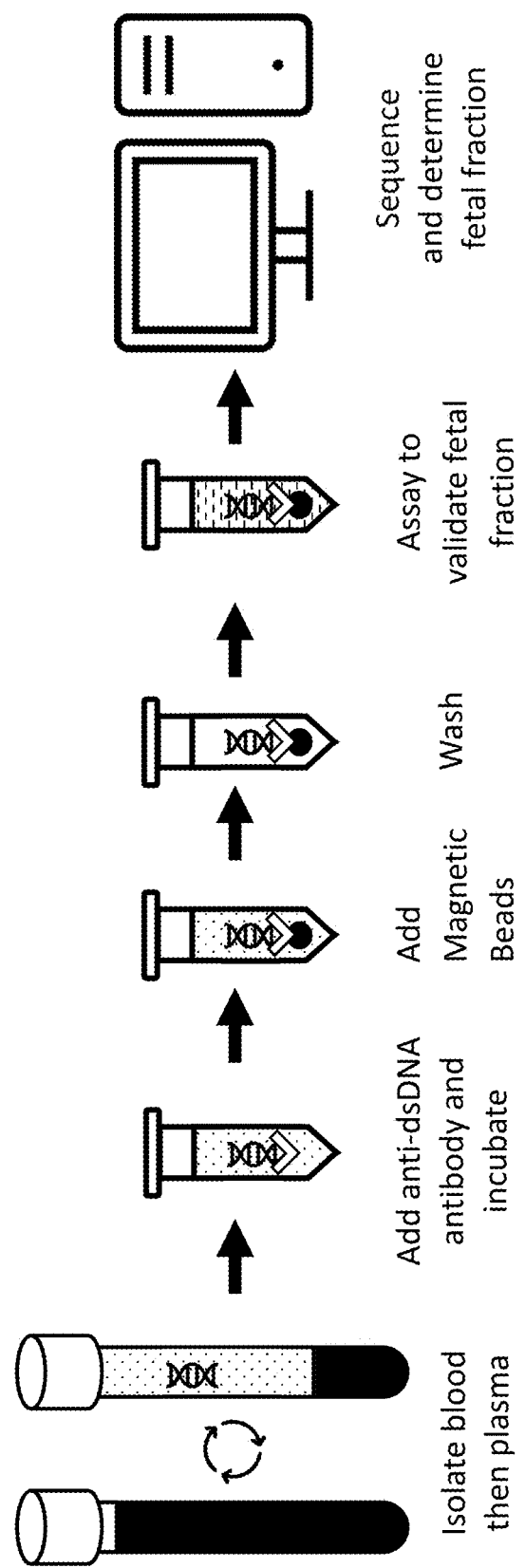
FIG. 1 shows an exemplary workflow of a method for enriching fetal cfDNA and suitable downstream steps (e.g., validating and determining the fetal fraction of cfDNA obtained).

In some aspects, provided herein are compositions and methods for isolating cell-free DNA from a sample, e.g., a plasma sample. In particular embodiments, the technology provides methods and compositions for capturing cell-free DNA from plasma, and analyzing the captured cell-free DNA, e.g., in a nucleic acid detection assay, without intervening alcohol precipitation, chaotrope treatment, or salt- or pH-mediated adsorption of the DNA to a matrix, e.g., a column matrix, filter, or particle.

In some embodiments, provided herein are different biochemical enrichment approaches for isolating membrane bound compartments in the plasma for subsequent cfDNA analysis. The present invention uses differential purification of membrane bound cell-free DNA to select for unique sources of DNA. In some embodiments, the specific detergent(s) used during the isolation of cfDNA allows for isolation of different membrane bound compartments. Membranes are differentially solubilized in various detergents as reported in Schuck et. al., Proc. Natl. Acad. Sci. USA 100:10, the entire contents of which are incorporated herein by reference. For example, using Triton X-100 solubilizes detergent sensitive membranes, but not membranes rich in cholesterol (e.g., detergent resistant membranes). Accordingly, using a detergent that solubilizes membranes without cholesterol enables selection for a unique DNA source from plasma. While cell-free DNA isolated from plasma is derived from the cell deaths of many cells in the body, fetal cell-free DNA has been shown to originate from Trophoblasts cells. By isolating membrane compartments from plasma, a selective isolation of cell-free DNA can result in a higher percentage of fetal cell-free DNA.

In some aspects, provided herein are compositions and methods for providing a preparation of cell-free DNA from a maternal sample in which the fraction of isolated cell-free DNA that is fetal DNA is increased or enriched.

In some aspects, provided herein are methods for isolating cfDNA from a sample comprising contacting the sample with an anti-dsDNA antibody, using Triton X-100 to solubilize membranes lacking cholesterol, and isolating cfDNA from the sample. The step of contacting the sample with an anti-dsDNA antibody is performed prior to isolating the cfDNA from the sample.

In some aspects, provided herein are compositions and methods for providing a preparation of cell-free DNA from a subject requiring assessment for one or more disease states. The disease state may be transplant rejection. For example, the compositions and methods described herein may be used to provide a preparation of cell-free DNA from a subject containing self and non-self (e.g., donor-derived) cfDNA. Such a preparation may be used in methods of assessing risk of transplant rejection in the subject. For example, levels of donor-derived cfDNA above a threshold value may be used to quantify risk of transplant rejection in the subject.

In some embodiments, the disease state may be cancer. For example, the compositions and methods described herein may be used to provide a preparation of cell-free DNA containing cfDNA derived from normal cellular turnover within the subject and tumor-derived cfDNA. The presence and/or amount of tumor-derived cfDNA may be used to diagnose and/or prognose cancer progression in the subject. In some embodiments, the presence and/or amount of tumor-derived cfDNA may be used to diagnose and/or prognose risk of cancer recurrence in the subject.

In some embodiments, the sample is a tissue sample. In some embodiments, the sample is a biological fluid. In some embodiments, the sample is urine, blood, serum, or plasma. In particular embodiments, the sample is a plasma sample. The sample may be obtained from a pregnant subject.

An "anti-dsDNA antibody" may be any suitable antibody that preferentially binds to double stranded DNA. In some embodiments, the anti-dsDNA antibody possesses a higher binding affinity for double stranded DNA compared to single stranded DNA (ssDNA). In some embodiments, the anti-dsDNA antibody possesses no detectable binding to ssDNA. In some embodiments, the anti-dsDNA antibody possesses no detectable binding to RNA. In some embodiments, the anti-dsDNA antibody may be purchased from a suitable vendor. An anti-dsDNA antibody may be of any form or preparation, e.g., it may be or comprise a natural antibody, a recombinant antibody, a fragment antibody, a monoclonal antibody, or a polyclonal antibody, or other variants of antibody forms or preparations.

In some aspects, the detergent(s) used in the immunoprecipitation step will permeabilize certain membranes, thus allowing the antibody to access and bind to the DNA previously occluded by the membrane. In particular embodiments, Triton X-100 (Millipore-Sigma catalog number 9002-93-1) is used as the detergent during the DNA isolation to permeabilize membranes without cholesterol. In particular embodiments, suitable detergents for permeabilization of membranes include SDS, saponin, CHAPS, Tween20, Brij 96, Brij 98, and Lubrol detergents. The use of such detergents may enable enhancement of fetal cfDNA found within compartments bordered by specific cell membrane types. For example, fetal cfDNA may be found within compartments bordered by membranes permeabilized by such detergents, e.g., cholesterol-free membranes.

In embodiments, the methods described herein may be used to capture circulating cfDNA. For example, the circulating cfDNA may be donor-derived cfDNA released from an allogeneic transplant. As another example, the circulating cfDNA may be tumor-derived cfDNA released from a cancerous tumor. In such embodiments, the anti-dsDNA antibody may effectively bind to the circulating cfDNA to form a DNA-antibody complex without the requirement for a specific detergent to be used in the cfDNA isolation step.

As used herein, anti-dsDNA antibody is distinct form antibodies that are specific for particular modifications of DNA, e.g., methylated bases. As used herein, anti-dsDNA antibodies refer to antibodies that bind to dsDNA regardless of methylation state. anti-dsDNA antibodies of the technology may also have strong reactivity with single-stranded DNA. For example, in some embodiments, Anti-ds DNA antibody [3519 DNA], Product No. ab27156 from Abcam, Discovery Drive, Cambridge Biomedical Campus, Cambridge, CB2 0AX, UK is used. This antibody is a mouse monoclonal antibody to dsDNA, with primary specificity to double stranded DNA, with measurements by immuno-CE yielding KD's of 0.71 µM and 0.09 µM, for the interaction of this antibody with ss- and dsDNA, respectively. Strong reactivity with both ss- and dsDNA has been observed on dotblots as well as very weak reactivity with RNA. The minimal size for DNA binding for this antibody is >16 bases.

Contacting the sample with the anti-dsDNA antibody may comprise incubating the sample with the antibody for a suitable duration of time under conditions that facilitate binding of the antibody to the double stranded DNA. For example, the sample may be incubated with the antibody for 1 minute to 24 hours. For example, the sample may be incubated with the antibody for 1 minute, 30 minutes, 1 hour, 2 hours, 3 hours, 4 hours, 5 hours, 10 hours, 12 hours, 24 hours, or 48 hours.

In some embodiments, the sample may be contacted with one or more suitable reagents prior to, concurrently with, or following contact with the anti-dsDNA antibody. These additional reagents may be contacted with the sample separately from the composition containing the anti-dsDNA antibody. Alternatively, one or more suitable additional reagents may be included in the composition containing the anti-dsDNA antibody. Suitable reagents include buffers, salts, detergents, preservatives, inhibitors, and the like. In some embodiments, such reagents are added to the sample after incubation with the anti-dsDNA antibody as part of a cfDNA isolation protocol.

Following contacting the sample with the anti-dsDNA antibody, cfDNA is isolated from the sample. For example, the anti-dsDNA antibody may bind to the cfDNA in the sample, thus creating a DNA-antibody complex. The DNA-antibody complex may be isolated (e.g. immunoprecipitated) from the sample. Subsequent processing steps (e.g. heating, denaturing during hybridization capture, etc.) may be employed to remove the antibody from the cfDNA to allow the enriched cfDNA to be used in downstream NIPT methods.

The cfDNA-antibody complex may be isolated from the sample by any suitable method. For example, the DNA-antibody complex may be isolated from the sample using an antibody binding protein which binds to the antibody in the complex. For example, the DNA-antibody complex may be isolated from the sample using an "antibody-binding reagent," e.g., an antibody-binding protein such as bacterial proteins such as protein A, protein G, protein A/G, or protein L. In some embodiments, the antibody-binding protein has affinity for an entity conjugated to the antibody. For example, the antibody may be biotinylated and the antibody binding protein may have affinity for biotin. For example, the antibody may be biotinylated and avidin/streptavidin may be used to isolate the DNA-antibody complex.

The antibody-binding protein may be immobilized on a suitable substrate/support. Suitable supports include solid supports (e.g., smooth metal, glass, quartz, plastic, silicon, wafers, carbon (e.g., diamond), and ceramic surfaces, etc.), as well as textured and porous materials. In some embodiments, the support is a bead (e.g. a paramagnetic or magnetic bead). Support materials also include, but are not limited to, gels, hydrogels, aerogels, rubbers, polymers, and other porous and/or non-rigid materials.

In some embodiments, cfDNA may be isolated using a commercially available kit for cfDNA isolation. Suitable kits are available through a variety of vendors, including ThermoFisher Scientific (e.g., MagMAX™ Cell-Free DNA Isolation Kit); Qiagen (e.g., QIAsymphony PAXgene Blood ccfDNA kit, QIAamp ccf/DNA/RNA kit, etc), and others. Suitable kits and protocols for using the same may be modified to optimize cfDNA enrichment.

In some embodiments, the methods provided herein result in an enriched concentration or amount of cell-free DNA compared to samples that are not contacted with an anti-dsDNA antibody prior to cfDNA isolation. The cell-free DNA may include self cfDNA, tumor-derived cfDNA, fetal cfDNA, and/or donor-derived cfDNA.

In some embodiments, the methods provided herein result in an enriched concentration or amount of cell-free fetal DNA compared to samples that are not contacted with an anti-dsDNA antibody prior to cfDNA isolation. DNA is wrapped up in proteins, thus preventing facile purification from plasma. Traditional approaches to cfDNA isolation break the DNA and protein apart using harsh solutions (chaotropic salts, pH, harsh detergents) to denature the proteins to release the DNA for subsequent purification using standard precipitation approaches (PEG, ethanol, etc.). In contrast, the approach described herein uses an anti-dsDNA antibody to bind the DNA, and subsequent immunoprecipitation steps pull the whole DNA-protein-antibody complex out of the plasma. Subsequent processing steps remove the protein and/or DNA from the complex, leaving the enriched cfDNA fraction. Without wishing to be bound by theory, it is possible that standard cfDNA isolation protocols may be sufficient for capture of maternal cfDNA, but incur notable loss of fetal cfDNA recovery, as fetal cfDNA fragments are known to be shorter than maternal cfDNA (see Chan et al., 2004, Clinical Chemistry 50:1 88-92, the entire contents of which are incorporated herein by reference). In contrast, the gentler methods described herein may be more effective at preventing loss of these shorter cfDNA fragments during processing steps. Without being bound by any particular mechanism of action or theory, it is contemplated that complete or partial disruption of detergent-sensitive membranes (but not detergent resistant membranes, such as lipid rafts), enriches fetal cfDNA during cfDNA purification from maternal plasma, in comparison to methods in which all membranes are disrupted prior to cfDNA isolation.

In some embodiments, further enrichment of the fetal fraction of cfDNA obtained by the methods described herein may be achieved by optimizing the cfDNA isolation step for fetal cfDNA. As described above, fetal cfDNA fragments are known to be shorter than maternal cfDNA fragments. Accordingly, size-based selection may preferentially select for cell-free fetal DNA compared to cell-free maternal DNA. Such size-based selection may be achieved by using different sized magnetic beads, as described in Hu et al., J Transl Med 2019 17:124, the entire contents of which is incorporated herein by reference.

In some embodiments, further enrichment of the fetal fraction of cfDNA obtained by the methods described herein may be achieved by repairing extracting cfDNA molecules prior to targeted sequencing. Fetal-derived cfDNA molecules are known to be shorter and more fragmented than the maternal fragments, and thus may possess more DNA damages. By repairing these damaged fetal cfDNA molecules, enrichment of fetal cfDNA may be further enhanced. Suitable methods for repair are described for example in Vong et al., Prenatal Diagnosis 2019 39: 88-99, the entire contents of which are incorporated herein by reference.

In some embodiments, the methods for enriching cfDNA described herein may be performed and the enriched cfDNA may be subsequently subjected a desired method genetic testing. In some embodiments, the isolated cfDNA may be subjected to a desired method for non-invasive prenatal testing (NIPT). NIPT is directed to the analysis of fetal cfDNA that circulates in the blood of a woman carrying the fetus in utero. Analysis of cell-free DNA in maternal blood can be used to assess the health of the fetus.

Genetic testing (including NIPT) may involve assessing the sample for one or more mutations. Genetic analysis may include analysis of any desired mutation, including base substitutions, insertions, deletions, translocations, or analysis of variations in copy numbers of specific nucleic acids sequences that may arise, e.g., from variations in chromosome number, gene copy number, expression level, etc. For example, the enriched cfDNA may be subjected to methods for analysis of variations in copy numbers of specific nucleic acids sequences that may arise, e.g., from variations in chromosome number, gene copy number, expression level, etc. For example, the enriched cfDNA may be employed in methods for assessing for chromosomal disorders caused by any chromosomal abnormality, including aneuploidy (e.g. presence of an extra copy of a chromosome or a missing copy of a chromosome); deletions or copied sections of a chromosome, variants in single genes (e.g. SNPs), and the like.

In some embodiments, genetic testing may involve assessing a sample of cfDNA for one or more mutations known to be associated with cancer. In some embodiments, genetic testing may involve assessing the sample for the presence and/or amount of non-self (e.g. donor-derived) cfDNA, such as for the assessment of transplant risk.

In particular embodiments, the technology described herein finds use in preparing isolated cell-free DNA and cell-free DNA enriched for fetal cfDNA for use with technologies including but not limited technologies described in U.S. Pat. No. 10,465,245, issued Nov. 5, 2019; WO/2017/020024 filed Feb. 2, 2017; WO/2017/083366, filed Nov. 9, 2016; WO 2017/087560, filed Nov. 16, 2016; WO 2018/094031, filed Nov. 16, 2017; WO 2019/195346, filed Apr. 2, 2019; and PCT Application Ser. No. PCT/US20/26456 of Sekedat, et al., filed Apr. 2, 2020; each of which is incorporated herein by reference in its entirety, for all purposes.

EXPERIMENTAL EXAMPLES

Example 1

This example provides examples of work-flows for enrichment and subsequent analysis of cfDNA, such as fetal cfDNA, from a sample such as a blood sample. An exemplary workflow schematic is shown in FIG. 1.

Sample Collection

Venous blood (approximately 20 mL) was collected and stored in a Streck blood collection tube (e.g. cell-free BCT tube) or alternative EDTA-containing blood collection tube. The sample was transported into a lab at ambient temperature and processed as follows:

Centrifuge blood at 2000×g for 20 minutes at room temperature to obtain a plasma fraction from the blood.

Transfer plasma into a new, sterile, nuclease-free polypropylene tube and centrifuge at 3220×g for 30 minutes.

Plasma was frozen at −80° C. until cfDNA enrichment was performed.

Cell-Free DNA (cfDNA) Isolation

Plasma was thawed on ice

2×IP Buffer (10 mL total final volume) was created as shown in Table 1.

TABLE 1

| Stock Concentration | Volume | Final Concentration (2×) |
|---|---|---|
| 1M TRIS pH 8.0 | 400 μL | 40 mM Tris |
| 5M NaCl | 550 μL | 274 mM NaCl |
| 100% Triton X-100 | 200 μL | 2% Triton X-100 |
| 500 mM EDTA | 80 μL | 4 mM EDTA |
| Roche HALT Protease Inhibitor | 200 μL | 2× Protease Inhibitor |

Equal volume of 2× IP buffer was added to the plasma sample and the tube was mixed by flicking.

1 μL of anti-ds DNA antibody was added to the tube (abcam catalog number ab27156)

20 μL of Protein G Beads magnetic beads was added to the tube

Tubes were incubated overnight in a heater shaker at 4° C. with shaking at 500 rpms Samples were washed 4 times in 1×IP Buffer. 1× Ampligase reaction buffer was added for the last wash (Ampligase 1× Reaction Buffer generally comprises: 20 mM Tris-HCl (pH 8.3), 25 mM KCl, 10 mM MgCl2, 0.5 mM NAD, and 0.01% Triton X-100.)

Beads were resuspended in 15 μL 1× Ampligase buffer.

Beads comprising captured DNA may be added directly to DNA assay methods, e.g., PCR, ligation assays, RCA, etc. MIP capture experiments described below show that the DNA can be analyzed without elution from the supports or treatment to remove antibodies or other proteins.

Following cfDNA enrichment, suitable methods may be performed to assess the cfDNA, such as methods for assess for mutations in cfDNA that may be indicative of the health of the fetus.

Note that the exact reagents and concentrations in Table 1 are only exemplary, and may be modified to optimize conditions for cfDNA enrichment. Alternative reagents (e.g. salts, buffers, inhibitors, detergents, etc.) and/or concentrations may be used.

Example 2

Figure 2:
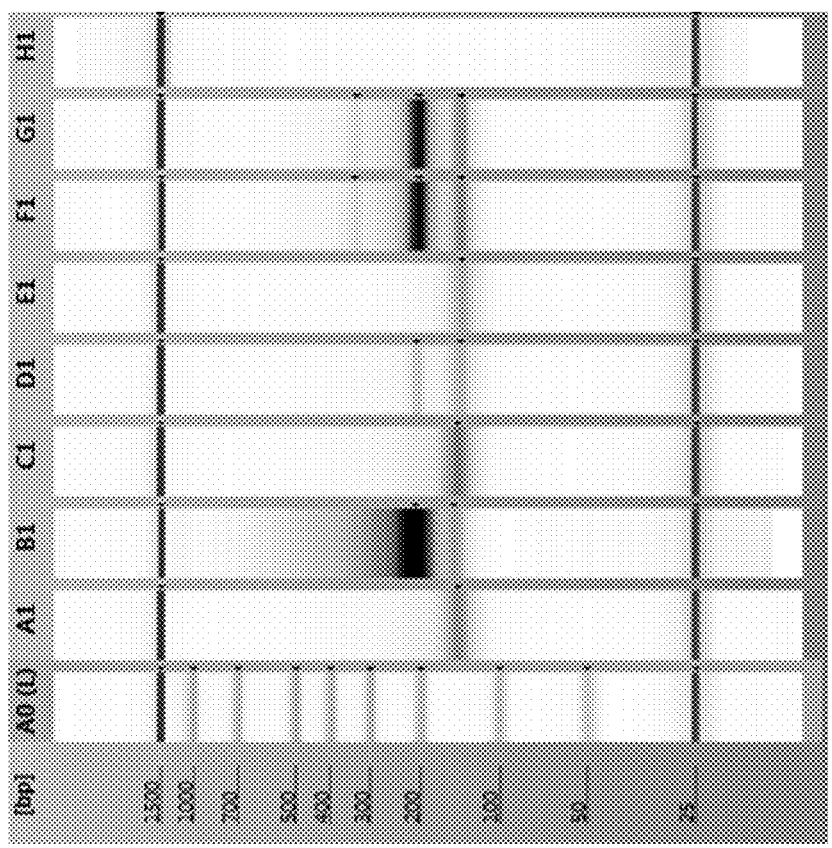
FIG. 2 shows an Agilent TapeStation (Agilent cat. num. 5067-5584) gel comparing DNA yield following different fetal cfDNA enrichment protocols using Triton X-100 as a detergent. The lanes are as follows:
A0—DNA Ladder
A1—no input cfDNA, subjected to the purification protocol described in J Med Screen, 2020 March; 27 (1):1-8, the entire contents of which are incorporated herein by reference. Subsequent hybridization, gap extension, ligation, and PCR amplification steps were performed as described. Amplified DNA was used as the template for the gel.
B1—cfDNA subjected to the same protocol used for lane A1. Input was 2 mL of cfDNA-containing plasma.
C1—cfDNA-containing sample (200 μL plasma) was incubated with anti-dsDNA antibody without subsequent immunoprecipitation with paramagnetic beads. Subsequent hybridization, gap extension, ligation, and PCR amplification steps were performed using protocol described above for lanes A1 (and B1), without the initial DynaBead™ cfDNA purification steps.
D1—cfDNA-containing sample (200 μL plasma) was purified following the protocol used in lane A1.
E1—control sample (no cfDNA input) incubated with anti-dsDNA antibody and immunoprecipitated using protein G paramagnetic beads (New England Biolabs, catalog number S1430S). Subsequent hybridization, gap extension, ligation, and PCR amplification steps were performed using protocol described above for lane A1, without the initial DynaBead™ cfDNA purification steps.
F1—cfDNA-containing sample (200 μL plasma) isolated from patient #1 was incubated with anti-dsDNA antibody and immunoprecipitated using protein G paramagnetic beads (New England Biolabs, catalog number S1430S). Subsequent hybridization, gap extension, ligation, and PCR amplification steps were performed using protocol described above for lane A1, without the initial DynaBead™ cfDNA purification steps.
G1—cfDNA-containing sample (200 μL plasma) isolated from patient #2 was incubated with anti-dsDNA antibody and immunoprecipitated using protein G paramagnetic beads (New England Biolabs, catalog number S1430S). Subsequent hybridization, gap extension, ligation, and PCR amplification steps were performed using protocol described above for lane A1, without the initial DynaBead™ cfDNA purification steps.

This example provides a comparison of cfDNA yield following subjecting samples to various cell-free DNA enrichment protocols. In particular, protocols with and without anti-dsDNA antibody incubation are compared. Results are shown in FIG. 2.

In particular, a comparison of lanes B1, D1, F1, and G1 reveal that incubation with anti-dsDNA antibody and subsequent immunoprecipitation with paramagnetic beads (e.g. protein G beads) produces sufficient cfDNA from only 200 μL of plasma. This is shown by the band at 200 bp, indicative of the molecular inversion probe that has captured the cfDNA, been ligated into a circle, and then PCR amplified as described in J Med Screen, 2020 March; 27 (1):1-8, the entire contents of which are incorporated herein by reference. The band at 150 bp is indicative of unused molecular inversion probe.

B1—Input was 2 mL plasma. No anti-dsDNA antibody incubation step was performed.

D1—Input was 200 μL plasma. No anti-dsDNA antibody incubation step was performed.

F1—cfDNA-containing sample (200 μL plasma) isolated from patient #1 was incubated with anti-dsDNA antibody and immunoprecipitated using protein G paramagnetic beads (New England Biolabs, catalog number S1430S). Subsequent hybridization, gap extension, ligation, and PCR amplification steps were performed.

G1—cfDNA-containing sample (200 μL plasma) isolated from patient #2 was incubated with anti-dsDNA antibody and immunoprecipitated using protein G paramagnetic beads (New England Biolabs, catalog number S1430S). Subsequent hybridization, gap extension, ligation, and PCR amplification steps were performed.

As shown, lanes F1 and G1 show a stronger band at 200 bp compared to lane D1. Each lane used the sample volume of plasma. Accordingly, incubation with anti-dsDNA antibody and immunoprecipitation with paramagnetic beads improves enrichment of cfDNA in the sample. This volume of input is about 1/10 the amount of plasma required to generate a similar signal without the anti-dsDNA incubation step (e.g., as shown in lane B1.)

Example 3

Figure 3:
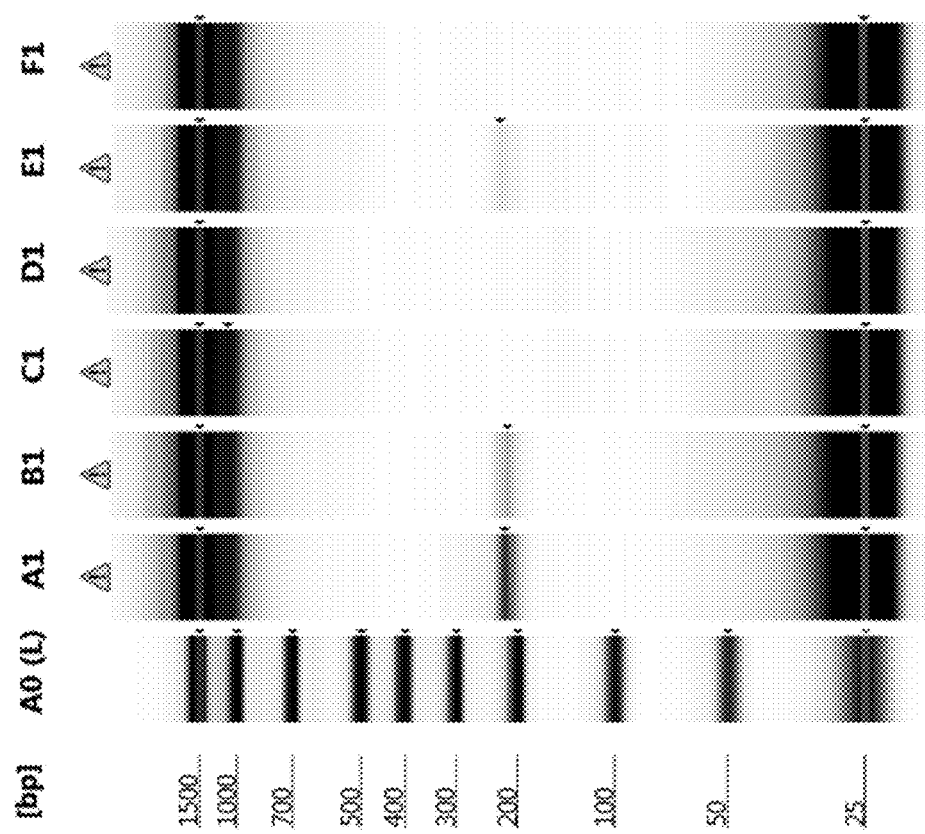
FIG. 3 shows am Agilent TapeStation (Agilent cat. num. 5067-5584) gel comparing DNA yield following different fetal cfDNA enrichment protocols using Triton X-100 as a detergent. For each lane, plasma was pooled from three individuals. Lanes are as follows:
A0—DNA Ladder
A1—2 mL plasma subjected to the purification protocol described in J Med Screen, 2020 March; 27 (1):1-8. Subsequent hybridization, gap extension, ligation, and PCR amplification steps were performed as described. Amplified DNA was used as the template for the gel.
B1—2 mL plasma subjected to the protocol described for lane A1, but with protein G and protein A beads spiked into the reaction.
C1—200 μL plasma incubated with anti-ssDNA antibody and immunoprecipitated with protein G beads. Subsequent hybridization, gap extension, ligation, and PCR amplification steps were performed as in lane A1.
D1—200 μL plasma incubated with anti-ssDNA antibody. No protein G immunoprecipitation step was performed. Subsequent hybridization, gap extension, ligation, and PCR amplification steps were performed as in lane A1.
E1—200 μL plasma incubated with anti-dsDNA antibody and immunoprecipitated with protein G beads. Subsequent hybridization, gap extension, ligation, and PCR amplification steps were performed as in lane A1.
F1—200 μL plasma incubated with anti-dsDNA antibody. No protein G immunoprecipitation step was performed. Subsequent hybridization, gap extension, ligation, and PCR amplification steps were performed as in lane A1.

This example provides a comparison of cfDNA yield following subjecting samples to various cell-free DNA enrichment protocols. In particular, protocols with and without anti-dsDNA antibody and anti-ssDNA antibody incubation are compared. Results are shown in FIG. 3. The dark bands at the top and bottom of the gel show the low and high molecular weight markers for the system. Taken together, the results show that incubation with an anti-dsDNA antibody, but not incubation with an anti-ssDNA antibody, results is enhanced isolation of cfDNA from the plasma sample. This is shown by the band at 200 bp, indicative of the molecular inversion probe that has captured the cfDNA, been ligated into a circle, and then PCR amplified as described in J Med Screen, 2020 March; 27 (1):1-8, the entire contents of which are incorporated herein by reference. In particular, the 200 bp band for lane E1 is comparable to the strength of the band in lane B1, with only 1/10 the input volume of plasma. Moreover, lane C1 shows no visible band, indicating that incubation with an anti-ssDNA antibody and protein G beads is not an effective means for immunoprecipitation of cfDNA.

A1—plasma subjected to the purification protocol described in J Med Screen, 2020 March; 27 (1):1-8. Subsequent hybridization, gap extension, ligation, and PCR amplification steps were performed as described. Amplified DNA was used as the template for the gel.

B1—plasma subjected to the protocol described for lane A1, but with protein G and protein A beads spiked into the reaction.

C1—plasma incubated with a ssDNA antibody and immunoprecipitated with protein G beads. Subsequent hybridization, gap extension, ligation, and PCR amplification steps were performed as in lane A1.

E1—plasma incubated with a dsDNA antibody and immunoprecipitated with protein G beads. Subsequent hybridization, gap extension, ligation, and PCR amplification steps were performed as in lane A1.

Example 4

This example provides a comparison of cfDNA yield following subjecting samples to various cell-free DNA enrichment protocols. In particular, protocols with and without anti-dsDNA antibody incubation are compared. Results are shown in FIG. 4.

The results shown in the "standard purification" row show values obtained using the method described in J Med Screen, 2020 March; 27 (1):1-8, the entire contents of which are incorporated herein by reference. Briefly, samples were isolated using a customized DynaMax cfDNA extraction protocol (Thermo Fisher Scientific; Waltham, MA, USA) adapted for a Microlab Star liquid handling system (Hamilton Robotics; Reno, NV, USA). Isolated cfDNA samples were eluted from the DynaBeads into a single low-bind 96-well polymerase chain reaction (PCR) plate (Eppendorf) for testing. Using the described MIP cfDNA Assay Protocol, the cfDNA sample is mixed with the identified capture probe and incubated in a thermal cycler to generate hybridized probe-cfDNA product. Modified MIP extension/ligation protocols were used to capture repeat sequences from cfDNA. The single stranded circular DNA generated from the capture protocol was used as template in a universal PCR reaction containing primers that bind to the MIP backbone. PCR product libraries were purified with Ampure XP beads (Agencourt AMPure XP, Beckman Coulter; Brea, CA, USA), sample concentrations were normalized to 1 ng/uL, and samples were pooled into a multiplexed sequencing library.

FIG. 4 shows three algorithms that can calculate the amount of fetal cfDNA in the assay sequencing results. The SNP approach looks at the SNP ratio of hundreds of known SNPs in the genome. The CHR Y approach determines the presence of chromosome Y in the sample, and thus is indicative entirely of male fetal DNA. The CHR X approach evaluates chromosome X in the sample. GOF refers to goodness of fit, or how well the sequencing results fit in the algorithm model for calculating the fetal fraction. Values closer to 1 indicate a better goodness of fit. The algorithms used were trained to fit the assay described in J Med Screen, 2020 March; 27 (1):1-8, so it is not surprising that the GOF value is slightly worse for the purification protocol using anti-dsDNA antibody described herein.

As the results shown in FIG. 4 were obtained using the same plasma sample, differences are thought to be due to difference in cfDNA preparation steps (e.g., antibody incubation and immunoprecipitation). The data was observed in three independent experiments, and suggests that incubation with an anti-dsDNA antibody improves enrichment of the fetal fraction of cfDNA.

All literature and similar materials cited in this application, including the publications described in the Bibliography above, and including but not limited to patents, patent applications, articles, books, treatises, and internet web pages, are expressly incorporated by reference in their entireties for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

I claim:

1. A composition comprising a solution comprising:
   a) antibody-DNA complexes that comprise:
      i) cell-free DNA from a blood product sample from a human subject, and
      ii) an exogenous anti-double-stranded DNA (anti-dsDNA) antibody that has reactivity to both single-stranded and double-stranded DNA.

2. The composition of claim 1, wherein the human subject is a pregnant human subject, and wherein the cell-free DNA comprises cell-free fetal DNA.

3. The composition of claim 1, wherein the human subject is suspected of having a tumor.

4. The composition of claim 1, wherein the antibody-DNA complexes comprise cell-free DNA comprising a plurality of dsDNA fragments having lengths of between 50 and 200 bp and having a size distribution comprising peaks at about 143 bp and 166 bp.

5. The composition of claim 1, wherein the solution comprises blood or a blood product from the human subject.

6. The composition of claim 5, wherein the blood product comprises serum or plasma.

7. The composition of claim 1, wherein the solution is substantially free of blood or blood product from the human subject such that any residual blood or blood product, if present, does not alter the function of the solution as compared to the solution if completely free of blood or blood product from the human subject.

8. The composition of claim 1, wherein the solution further comprises one or more of:
   b) a buffer;
   c) a detergent;
   d) a preservative;
   e) a protease inhibitor; and
   f) a nuclease inhibitor.

9. The composition of claim 1, wherein the solution comprises a reaction mixture.

10. The composition of claim 9, wherein the reaction mixture comprises at least one nucleic acid-modifying enzyme selected from a nucleic acid polymerase, a nuclease, and a ligase.

11. The composition of claim 1, wherein the solution further comprises:
    b) an antibody-binding reagent.

12. The composition of claim 11, wherein the antibody-binding reagent comprises a protein selected from protein A, protein G, protein A/G, and protein L.

13. The composition of claim 12, wherein the antibody-binding reagent comprises one or more beads.

14. The composition of claim 13, wherein the one or more beads comprises one or more paramagnetic beads.

* * * * *